United States Patent
Nair et al.

(10) Patent No.: US 8,068,660 B2
(45) Date of Patent: Nov. 29, 2011

(54) CHARACTERIZING VISION SYSTEMS

(75) Inventors: Dinesh R. Nair, Austin, TX (US);
Nicolas Vazquez, Austin, TX (US);
Robert J. B. Giesen, Austin, TX (US);
Joshua B. Keeler, Austin, TX (US);
Bruce Smyth, Hollis, NH (US)

(73) Assignee: National Instruments Corporation, Austin, TX (US)

( * ) Notice: Subject to any disclaimer, the term of this patent is extended or adjusted under 35 U.S.C. 154(b) by 772 days.

(21) Appl. No.: 12/127,231

(22) Filed: May 27, 2008

(65) Prior Publication Data
US 2009/0297042 A1    Dec. 3, 2009

(51) Int. Cl.
*G06K 9/00* (2006.01)
(52) U.S. Cl. ....................................... 382/141
(58) Field of Classification Search ........... 382/141–154
See application file for complete search history.

(56) References Cited

U.S. PATENT DOCUMENTS

| | | | |
|---|---|---|---|
| 2003/0007690 A1 * | 1/2003 | Rajagopal et al. | 382/209 |
| 2003/0179922 A1 * | 9/2003 | Peters et al. | 382/153 |
| 2006/0204121 A1 * | 9/2006 | Bryll | 382/255 |
| 2007/0146491 A1 | 6/2007 | Tremblay et al. | |

* cited by examiner

*Primary Examiner* — Michael P Stafira
(74) *Attorney, Agent, or Firm* — Meyertons Hood Kivlin Kowert & Goetzel, P.C.; Jeffrey C. Hood; Joel L. Stevens

(57) ABSTRACT

System and method for characterizing vision systems. A multi-dimensional condition space is provided, each dimension representing a respective condition axis, where each point in the condition space specifies a set of conditions under which a vision system may operate. An image is provided. The condition space is sampled according to a pseudo-random sequence, e.g., a low-discrepancy sequence, to determine a plurality of test conditions usable to characterize the vision system, where each test condition corresponds to a respective set of conditions. A plurality of test images corresponding to the plurality of test conditions are generated based on the image, e.g., by applying image processing functions to the image that simulate the test conditions. A vision inspection is performed on each of the plurality of test images to generate respective test results, and the test results are analyzed to determine conditions under which the vision system operates correctly.

37 Claims, 23 Drawing Sheets

Camera Geometry

Camera Position

Look At Position

Camera Pan

Camera Rotation

Lighting

Brightness

Contrast

Gamma

Motion Blur

Generated by movement during exposure

Length of the Blur

Angle of the Blur

Noise

Type
- Uniform
- Gaussian
- Impulse (Salt and Pepper)

Standard Deviation

Amount

Fig. 8

CHARACTERIZING VISION SYSTEMS

FIELD OF THE INVENTION

The present invention relates to the machine vision, and more particularly to a system and method for characterizing vision systems.

DESCRIPTION OF THE RELATED ART

Machine vision is an increasingly important technology in many areas of endeavor, such as manufacturing, quality control, security, and research, among others. However, theoretical or ideal conditions under which a vision system may be specified may be quite different from actual or field conditions under which the vision system operates in practice, i.e., in the real world.

This fact is illustrated in FIG. 1A, which shows an idealized image (left) and a more realistic example of an image from practice (right), according to the prior art. As may be seen, the "practice" image is influenced by various conditions (including vision system parameters) that are not a factor in the "theory" image. For example, FIG. 1B illustrates an exemplary vision system examining a circuit board. The performance of a vision system may be significantly degraded from the ideal case depending on the particular attributes of the vision system and conditions under which it operates, such as, for example, resolution, field of view, distance, lighting, camera position, depth of field, and sensor size, among others.

Verification and validation of a machine vision system is a critical step in building robust and reliable systems. The goal of the step or process is to test the machine vision system under different scenarios and parameter values that it is expected to function under and verify that the system behaves properly. More generally, vision systems may be tested against a broad variety of conditions and characterized by determining the conditions under which they operate correctly. A span of different conditions (including parameters) under which a vision system could potentially operate may be referred to as a "condition space", although other terms may also be used to refer to the same concept. In this condition space, each point represents a set of conditions under which a vision system may operate (and be tested). However, the number of variations and combinations possible increases dramatically with the number of parameters, and so a brute force approach to testing the system under all conditions is not feasible. In reality it is very difficult for a vision system integrator to physically mimic all the variations that can take place on the production line.

Prior art analysis and characterization of vision systems has typically been limited to testing the system according to a uniform sampling of each dimension of a condition space independently, which ignores synergistic effects among the parameters. Higher dimensional condition spaces, e.g., 2 or more dimensions, have not heretofore been analyzed for characterization of vision systems, primarily due to the rapid increases in complexity and commensurate computational resources required.

Thus, improved systems and methods for characterizing vision systems are required.

SUMMARY OF THE INVENTION

Various embodiments of a system and method for characterizing vision systems are presented below.

A multi-dimensional condition space may be provided, where each dimension represents a respective condition axis, and where each point in the condition space specifies set of conditions under which a vision system may operate. For example, the condition axes may include, but are not limited to, axes related to image object geometry, camera geometry, lighting, focus blur, motion blur, and/or noise. For example, condition axes related to image object geometry may include axes for one or more of: object scale, object rotation, or object offset, among others. Exemplary condition axes related to camera geometry may include axes for one or more of: camera position, look at position, camera pan, or camera rotation, among others. Note that the effects of camera geometry may be quite similar to those of image object geometry, although the causes and remedies are distinctly different-specifically, camera movement, position, and orientation, versus those of the object being inspected.

Exemplary condition axes related to lighting may include axes for one or more of brightness, contrast, or gamma, among others. Exemplary condition axes related to motion blur may include axes for length of blur and/or angle of blur. As is well known, motion blur is generated by movement during exposure, e.g., during the creation of the image. Exemplary condition axes related to noise may include axes for one or more of: noise type, e.g., uniform, Gaussian, and/or impulse (i.e., "salt and papper"), standard deviation, or amount of noise, among others. It should be noted that the conditions and effects described are meant to be exemplary only, and that other conditions and effects may be accommodated as desired.

In preferred embodiments, a graphical user interface (GUI) may be provided whereby the condition space may be specified. For example, the GUI may allow a user to configure bounds for condition axes to limit the size of the searchable space, sampling schemes, e.g., number of samples, sampling algorithm, and so forth. In one embodiment, the GUI may allow a user to specify which condition axes to include in the condition space, as well as ranges, i.e., upper and lower bounds, for each axis. Note that in some embodiments, default values may be provided as desired, e.g., defining a default condition space. The GUI may also allow the user to specify an input image, an output directory to which results may be stored, output image options, number of samples, and/or progress indicators, although other GUI elements may be included as desired. The GUI may also include a results area or tab whereby results may be displayed. Note that these condition bounds or ranges may be considered to be tolerance specifications for a vision system, where, for example, it is desired to determine what tolerances are required that result in robust operation of the vision system. Thus, in some embodiments, a GUI may be used to specify simulation of different imaging effects.

An image may be provided. This image is preferably representative of real-world images/image-objects to which the vision system being characterized will be applied, e.g., an image of a circuit board produced in a manufacturing plant that will utilize the vision system, a human face to be automatically recognized, etc. As described above, in one embodiment, a GUI may be used to specify this image.

The condition space may be sampled. There are a variety of sampling schemes that may be used to sample the condition space, where the particular scheme used may be selected based on attributes of the condition space or more generally, on the nature of the object being inspected or resource limitations, e.g., disk space, CPU, etc. For example, in one embodiment, the condition space may be of three or more dimensions, and any sampling scheme of the condition space may be used as desired, e.g., uniform sampling, random sampling, pseudo-random sampling, sampling according to a low discrepancy sequence, e.g., a Halton sequence, and so forth, as desired. In another exemplary embodiment, the condition space may be of two or more dimensions, and a sampling scheme based on a pseudo-random sequence, e.g., a low discrepancy sequence may be used, although it should be noted that in other embodiments, any sampling scheme may be used as desired.

Thus, in preferred embodiments, the condition space may be sampled according to a pseudo-random, e.g., low discrepancy, sequence to determine a plurality of test conditions usable to characterize the vision system, where each test condition corresponds to a respective set of conditions. In other words, each test condition includes parameter values for each axis of the condition space, and may thus define a set of conditions under which the vision system may inspect an image or image object.

A plurality of test images corresponding to the plurality of test conditions may be generated based on the image; i.e., each test condition may be used to generate a respective test image that reflects the effects of the test condition. Thus, the plurality of test images may provide a broad spectrum of vision inspection problems that may be used to characterize performance of a vision system.

In some embodiments, one or more of the test conditions may be implemented by modifying the vision system, e.g., by moving the camera and/or target, changing the focus of the camera lens, changing the lighting, and so forth. However, note that in general, it would not be practical or efficient to generate all the test images by actually modifying a vision system per the sample point conditions. Thus, in preferred embodiments, generating a plurality of test images corresponding to the plurality of test conditions based on the image may include generating the plurality of test images by applying image processing functions to the image that simulate the plurality of test conditions. Thus, the above-mentioned conditions may be simulated and applied to the original image to produce effects that degrade the quality of the image, thus generating the test images.

A vision inspection may be performed on each of the plurality of test images to generate respective test results. In other words, the vision system to be characterized may perform vision inspections on the test images and generate results, e.g., indicating whether the inspection passed or failed. In some embodiments, the sampling and the vision inspections may be performed conjunctively. For example, in some embodiments, the sampling the condition space, generating the plurality of test images, and performing a vision inspection on each of the plurality of test images may include: for each of a plurality of iterations: a) sampling the condition space to generate a condition point, b) generating a test image based on the condition point, c) performing a vision inspection on the test image, d) if the vision inspection fails, performing a)-c) for one or more condition points in a specified neighborhood of the condition point to determine a point for which the vision inspection passes. Thus, in some embodiments, based on the inspection results for a condition (point in the condition space), further testing may be performed in the neighbor of that condition/point to more precisely determine the boundary between a region of robustness and a region where inspection results may be unreliable.

In addition to, or instead of, the above, in some embodiments, the sampling the condition space, generating the plurality of test images, and performing a vision inspection on each of the plurality of test images may include: for each of a plurality of iterations: a) sampling the condition space to generate a condition point, b) generating a test image based on the condition point, c) performing a vision inspection on the test image, d) if the vision inspection fails, modifying parameters of the vision inspection (which may include modifying parameters of the vision system itself) and performing a)-c) in an iterative manner until the vision inspection passes. Thus, in some embodiments, the vision system/vision inspection may be "tuned" or otherwise modified, e.g., incrementally, to determine the boundaries of robust operation.

Finally, the test results may be analyzed to determine analysis results, specifically, conditions under which the vision inspection operates correctly. For example, the test results may be plotted or otherwise characterized to indicate the regions of the condition space that represent conditions under which the vision system (the vision inspection) operates correctly, i.e., passes images that should pass (and/or conversely, fails images that should fail), operates robustly. In one embodiment, the analyzing may include determining the fraction of passes of the vision inspection within the condition space, e.g., determining that 85% of the specified condition space results in correct inspections by the vision system, e.g., the vision system passes images that should pass under 85% of the specified conditions. As a more sophisticated example, in one embodiment, the analyzing may include determining a largest convex hull in the condition space specifying conditions under which the vision system is robust, i.e., under which vision inspections by the vision system will pass within a specified tolerance, e.g., where the vision system will correctly pass 98% of "matching" images or objects. Note, however, that any other type of analysis may be performed as desired, the above examples being exemplary only. Thus, the test results may be analyzed to characterize the vision system, i.e., to determine under what conditions the vision system may be expected to operate in a robust manner, meaning that images that should pass will pass, and those that shouldn't will not, at least to within some specified error or tolerance.

Once the test results have been analyzed, and the conditions under which the vision inspection operates correctly determined, the analysis results (the "pass" conditions) may be stored and/or output to a display. For example, in one embodiment, the maximal convex hull may be presented graphically, e.g., in the case where the condition space has high dimensionality, as one or more projections of a high-dimensional convex hull. As other examples, the analysis results may be represented in tabular fashion, as a collection of ranges, etc., as desired.

In one embodiment, the analysis results may be used to tune the vision system, e.g., the various physical parameters of the vision system may be adjusted or even reengineered to decrease tolerance levels of the various parameters to fall within the determined passing conditions. For example, if the camera's rotational freedom exceeds the angular conditions under which the inspection process is robust, the camera's motion control platform may be modified or configured to avoid operating outside the specified bounds for that parameter. Inputs to the process include the original image, system tolerances, which refer to the bounds of the condition space, and the machine vision inspection process itself. The modeling and simulation process generates the test images upon which the machine vision inspection is applied, which then produces test results which are input to an analysis process (and analyzed).

Thus, the robustness and reliability of a machine vision system may be determined based on simulated vision system conditions, and their effects on a template image. In determining robustness, the user is interested in determining how much variation in the image the machine vision inspection can tolerate and still operate correctly. Alternatively, the user may wish to determine the settings of the parameters for each imaging effect beyond which the machine vision inspection will fail (for an image that should pass).

Thus, embodiments of the invention may provide an intelligent method to search a multidimensional space of image variations to find the region in this multidimensional space within which the machine vision system will work robustly, i.e., where variations in the imaging conditions will not affect the inspection results, and may further be used to improve the performance and reliability of vision systems.

BRIEF DESCRIPTION OF THE DRAWINGS

A better understanding of the present invention can be obtained when the following detailed description of the preferred embodiment is considered in conjunction with the following drawings, in which:

FIG. 8 illustrates an exemplary graphical user interface for specifying a condition space and vision system characterization operations, according to one embodiment;

Figure 1A:
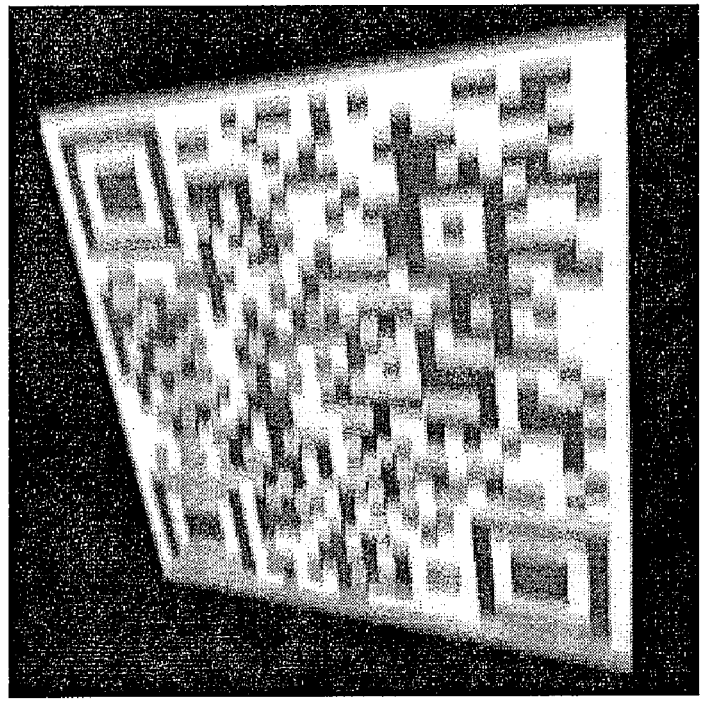
FIG. 1A illustrates examples of an image in theory and in practice, according to the prior art.
Figure 1A:
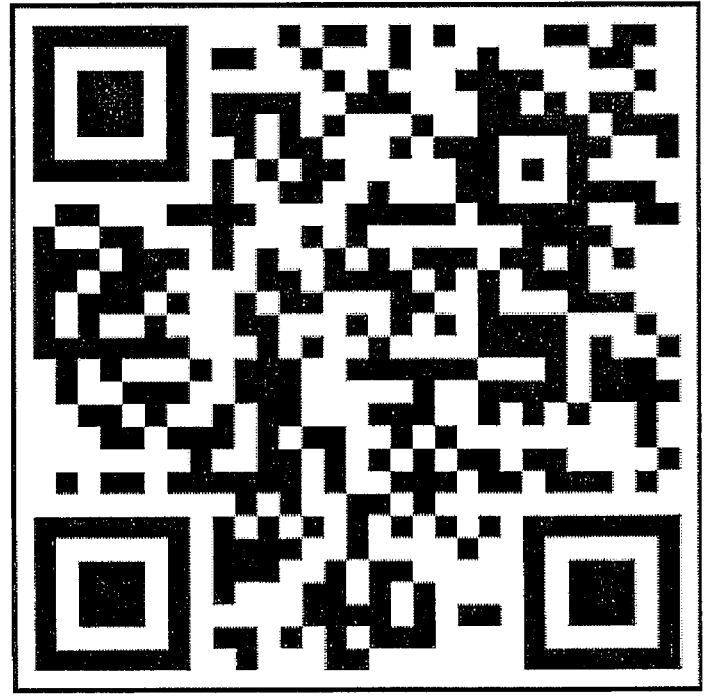
Figure 1B:
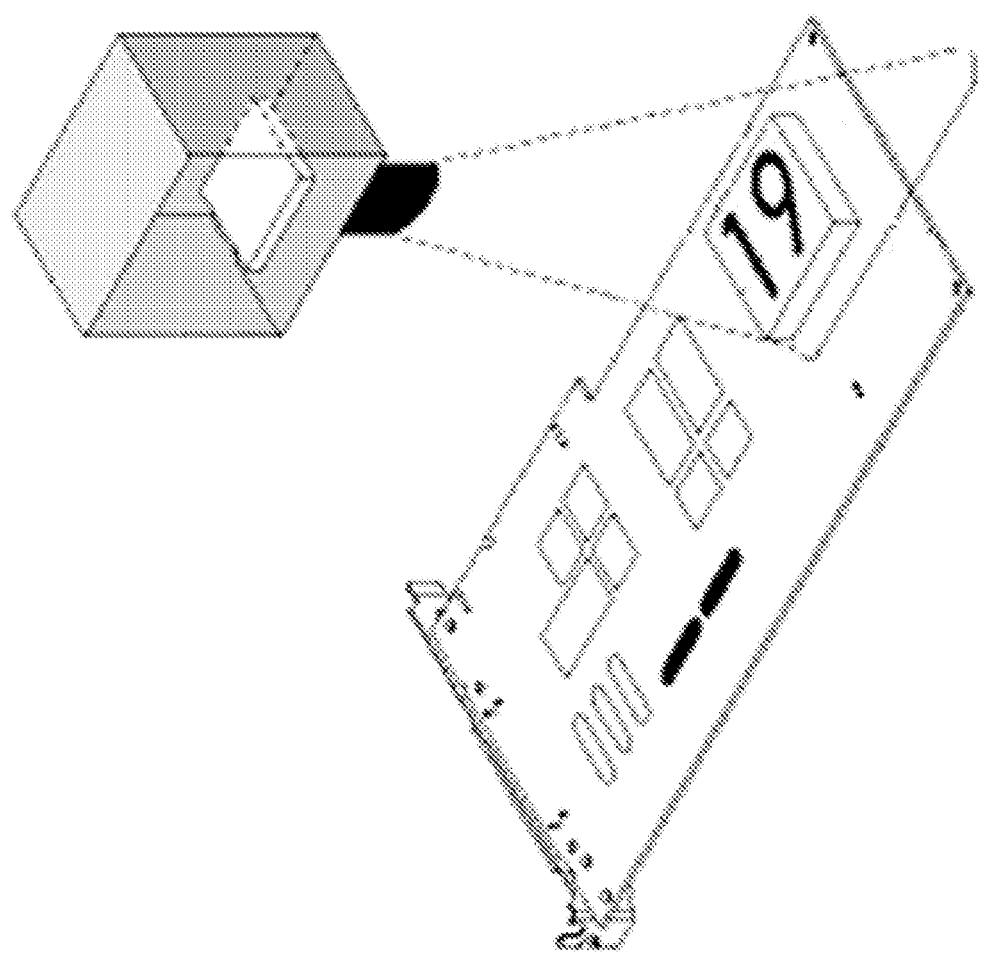
FIG. 1B illustrates an exemplary vision system, according to the prior art.

While the invention is susceptible to various modifications and alternative forms, specific embodiments thereof are shown by way of example in the drawings and are herein described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

Incorporation by Reference

The following references are hereby incorporated by reference in their entirety as though fully and completely set forth herein:

U.S. Pat. No. 6,959,104, titled "System and Method for Scanning a Region Using a Low Discrepancy Sequence", filed Jun. 8, 2001, whose inventors were Ram Rajagopal, Lothar Wenzel, and Dinesh Nair.

U.S. Pat. No. 6,917,710, titled "System and Method for Scanning a Region Using a Low Discrepancy Curve", filed Jun. 8, 2001, whose inventors were Ram Rajagopal, Lothar Wenzel, and Dinesh Nair.

Terms

The following is a glossary of terms used in the present application:

Memory Medium—Any of various types of memory devices or storage devices. The term "memory medium" is intended to include an installation medium, e.g., a CD-ROM, floppy disks 104, or tape device; a computer system memory or random access memory such as DRAM, DDR RAM, SRAM, EDO RAM, Rambus RAM, etc.; or a non-volatile memory such as a magnetic media, e.g., a hard drive, or optical storage. The memory medium may comprise other types of memory as well, or combinations thereof. In addition, the memory medium may be located in a first computer in which the programs are executed, and/or may be located in a second different computer which connects to the first computer over a network, such as the Internet. In the latter instance, the second computer may provide program instructions to the first computer for execution. The term "memory medium" may include two or more memory mediums which may reside in different locations, e.g., in different computers that are connected over a network.

Carrier Medium—a memory medium as described above, as well as a physical transmission medium, such as a bus, network, and/or other physical transmission medium that conveys signals such as electrical, electromagnetic, or digital signals.

Programmable Hardware Element—includes various hardware devices comprising multiple programmable function blocks connected via a programmable interconnect. Examples include FPGAs (Field Programmable Gate Arrays), PLDs (Programmable Logic Devices), FPOAs (Field Programmable Object Arrays), and CPLDs (Complex PLDs). The programmable function blocks may range from fine grained (combinatorial logic or look up tables) to coarse grained (arithmetic logic units or processor cores). A programmable hardware element may also be referred to as "reconfigurable logic".

Program—the term "program" is intended to have the full breadth of its ordinary meaning. The term "program" includes 1) a software program which may be stored in a memory and is executable by a processor or 2) a hardware configuration program useable for configuring a programmable hardware element.

Software Program—the term "software program" is intended to have the full breadth of its ordinary meaning, and includes any type of program instructions, code, script and/or data, or combinations thereof, that may be stored in a memory medium and executed by a processor. Exemplary software programs include programs written in text-based programming languages, such as C, C++, PASCAL, FORTRAN, COBOL, JAVA, assembly language, etc.; graphical programs (programs written in graphical programming languages); assembly language programs; programs that have been compiled to machine language; scripts; and other types of executable software. A software program may comprise two or more software programs that interoperate in some manner. Note that various embodiments described herein may be implemented by a computer or software program. A software program may be stored as program instructions on a memory medium.

Hardware Configuration Program—a program, e.g., a netlist or bit file, that can be used to program or configure a programmable hardware element.

Graphical Program—A program comprising a plurality of interconnected nodes or icons, wherein the plurality of interconnected nodes or icons visually indicate functionality of the program. Graphical function nodes may also be referred to as blocks.

The following provides examples of various aspects of graphical programs. The following examples and discussion are not intended to limit the above definition of graphical program, but rather provide examples of what the term "graphical program" encompasses:

The nodes in a graphical program may be connected in one or more of a data flow, control flow, and/or execution flow format. The nodes may also be connected in a "signal flow" format, which is a subset of data flow.

Exemplary graphical program development environments which may be used to create graphical programs include LabVIEW®, DasyLab™, DiaDem™ and Matrixx/SystemBuild™ from National Instruments, Simulink® from the MathWorks, VEE™ from Agilent, WiT™ from Coreco, Vision Program Manager™ from PPT Vision, SoftWIRE™ from Measurement Computing, Sanscript™ from Northwoods Software, Khoros™ from Khoral Research, SnapMaster™ from HEM Data, VisSim™ from Visual Solutions, ObjectBench™ by SES (Scientific and Engineering Software), and VisiDAQ™ from Advantech, among others.

The term "graphical program" includes models or block diagrams created in graphical modeling environments, wherein the model or block diagram comprises interconnected blocks (i.e., nodes) or icons that visually indicate operation of the model or block diagram; exemplary graphical modeling environments include Simulink®, SystemBuild™, VisSim™, Hypersignal Block Diagram™, etc.

A graphical program may be represented in the memory of the computer system as data structures and/or program instructions. The graphical program, e.g., these data structures and/or program instructions, may be compiled or interpreted to produce machine language that accomplishes the desired method or process as shown in the graphical program.

Input data to a graphical program may be received from any of various sources, such as from a device, unit under test, a process being measured or controlled, another computer program, a database, or from a file. Also, a user may input data to a graphical program or virtual instrument using a graphical user interface, e.g., a front panel.

A graphical program may optionally have a GUI associated with the graphical program. In this case, the plurality of interconnected blocks or nodes are often referred to as the block diagram portion of the graphical program.

Node—In the context of a graphical program, an element that may be included in a graphical program. The graphical program nodes (or simply nodes) in a graphical program may also be referred to as blocks. A node may have an associated icon that represents the node in the graphical program, as well as underlying code and/or data that implements functionality of the node. Exemplary nodes (or blocks) include function nodes, sub-program nodes, terminal nodes, structure nodes, etc. Nodes may be connected together in a graphical program by connection icons or wires.

Graphical Data Flow Program (or Graphical Data Flow Diagram)—A graphical program or diagram comprising a plurality of interconnected nodes (blocks), wherein at least a subset of the connections among the nodes visually indicate that data produced by one node is used by another node. A LabVIEW VI is one example of a graphical data flow program. A Simulink block diagram is another example of a graphical data flow program.

Graphical User Interface—this term is intended to have the full breadth of its ordinary meaning. The term "Graphical User Interface" is often abbreviated to "GUI". A GUI may comprise only one or more input GUI elements, only one or more output GUI elements, or both input and output GUI elements.

The following provides examples of various aspects of GUIs. The following examples and discussion are not intended to limit the ordinary meaning of GUI, but rather provide examples of what the term "graphical user interface" encompasses:

A GUI may comprise a single window having one or more GUI Elements, or may comprise a plurality of individual GUI Elements (or individual windows each having one or more GUI Elements), wherein the individual GUI Elements or windows may optionally be tiled together.

A GUI may be associated with a graphical program. In this instance, various mechanisms may be used to connect GUI Elements in the GUI with nodes in the graphical program. For example, when Input Controls and Output Indicators are created in the GUI, corresponding nodes (e.g., terminals) may be automatically created in the graphical program or block diagram. Alternatively, the user can place terminal nodes in the block diagram which may cause the display of corresponding GUI Elements front panel objects in the GUI, either at edit time or later at run time. As another example, the GUI may comprise GUI Elements embedded in the block diagram portion of the graphical program.

Front Panel—A Graphical User Interface that includes input controls and output indicators, and which enables a user to interactively control or manipulate the input being provided to a program, and view output of the program, while the program is executing.

A front panel is a type of GUI. A front panel may be associated with a graphical program as described above.

In an instrumentation application, the front panel can be analogized to the front panel of an instrument. In an industrial automation application the front panel can be analogized to the MMI (Man Machine Interface) of a device. The user may adjust the controls on the front panel to affect the input and view the output on the respective indicators.

Graphical User Interface Element—an element of a graphical user interface, such as for providing input or displaying output. Exemplary graphical user interface elements comprise input controls and output indicators.

Input Control—a graphical user interface element for providing user input to a program. An input control displays the value input the by the user and is capable of being manipulated at the discretion of the user. Exemplary input controls comprise dials, knobs, sliders, input text boxes, etc.

Output Indicator—a graphical user interface element for displaying output from a program. Exemplary output indicators include charts, graphs, gauges, output text boxes, numeric displays, etc. An output indicator is sometimes referred to as an "output control".

Computer System—any of various types of computing or processing systems, including a personal computer system (PC), mainframe computer system, workstation, network appliance, Internet appliance, personal digital assistant (PDA), television system, grid computing system, or other device or combinations of devices. In general, the term "computer system" can be broadly defined to encompass any device (or combination of devices) having at least one processor that executes instructions from a memory medium.

Measurement Device—includes instruments, data acquisition devices, smart sensors, and any of various types of devices that are operable to acquire and/or store data. A measurement device may also optionally be further operable to analyze or process the acquired or stored data. Examples of a measurement device include an instrument, such as a traditional stand-alone "box" instrument, a computer-based instrument (instrument on a card) or external instrument, a data acquisition card, a device external to a computer that operates similarly to a data acquisition card, a smart sensor, one or more DAQ or measurement cards or modules in a chassis, an image acquisition device, such as an image acquisition (or machine vision) card (also called a video capture board) or smart camera, a motion control device, a robot having machine vision, and other similar types of devices. Exemplary "stand-alone" instruments include oscilloscopes, multimeters, signal analyzers, arbitrary waveform generators, spectroscopes, and similar measurement, test, or automation instruments.

A measurement device may be further operable to perform control functions, e.g., in response to analysis of the acquired or stored data. For example, the measurement device may send a control signal to an external system, such as a motion control system or to a sensor, in response to particular data. A measurement device may also be operable to perform automation functions, i.e., may receive and analyze data, and issue automation control signals in response.

Subset—in a set having N elements, the term "subset" comprises any combination of one or more of the elements, up to and including the full set of N elements. For example, a subset of a plurality of icons may be any one icon of the plurality of the icons, any combination of one or more of the icons, or all of the icons in the plurality of icons. Thus, a subset of an entity may refer to any single element of the entity as well as any portion up to and including the entirety of the entity.

Figure 2A:
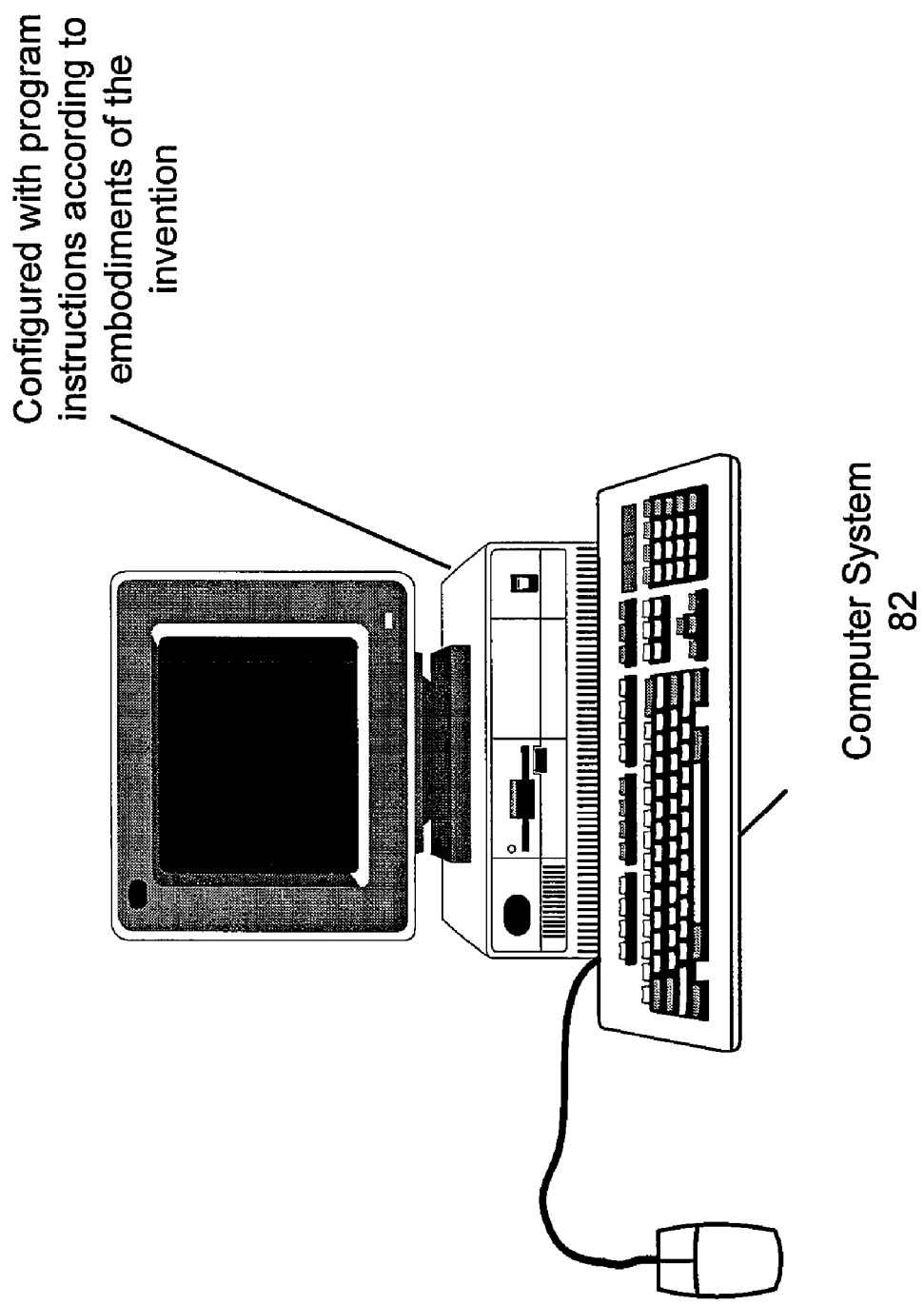
FIG. 2A illustrates a computer system configured to implement embodiments of the present invention.

FIG. 2A—Computer System

FIG. 2A illustrates a computer system 82 configured to implement embodiments of the present invention. One embodiment of a method for characterizing vision systems is described below. Some embodiments of the present invention may be implemented by software programs, i.e., via program instructions.

As shown in FIG. 2A, the computer system 82 may include a display device operable to display a graphical user interface for one or more programs of the present invention. The graphical user interface may comprise any type of graphical user interface, e.g., depending on the computing platform.

The computer system 82 may include at least one memory medium on which one or more computer programs or software components according to one embodiment of the present invention may be stored. For example, the memory medium may store one or more programs which are executable to perform the methods described herein. Additionally, the memory medium may store a programming development environment application used to create and/or execute such programs, as well as data, e.g., image data, configuration data, etc. The memory medium may also store operating system software, as well as other software for operation of the computer system. Various embodiments further include receiving or storing instructions and/or data implemented in accordance with the foregoing description upon a carrier medium.

Figure 2B:
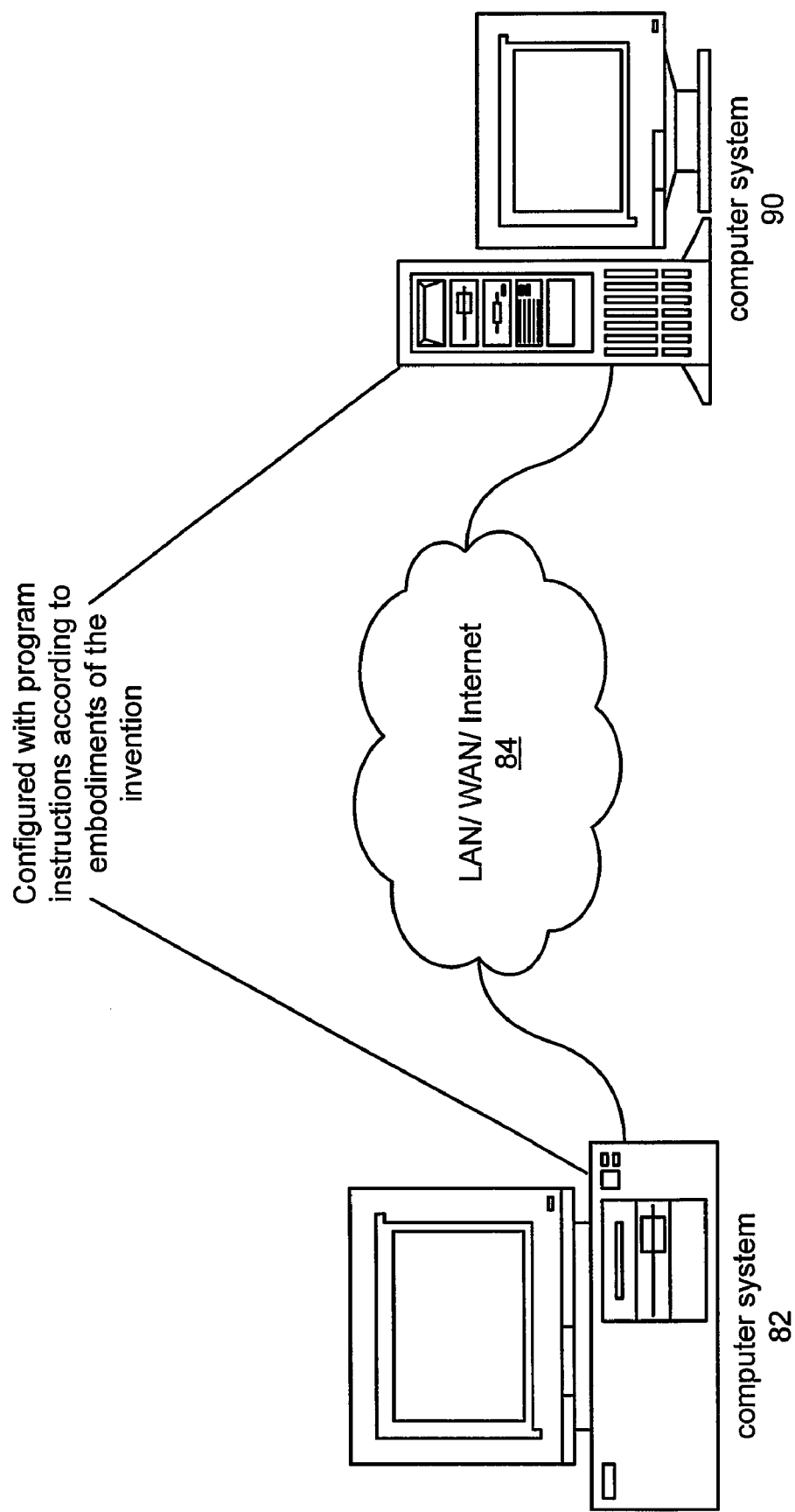
FIG. 2B illustrates a network system comprising two or more computer systems that may implement an embodiment of the present invention.

FIG. 2B—Computer Network

FIG. 2B illustrates a system including a first computer system 82 that is coupled to a second computer system 90. The computer system 82 may be coupled via a network 84 (or a computer bus) to the second computer system 90. The computer systems 82 and 90 may each be any of various types, as desired. The network 84 can also be any of various types, including a LAN (local area network), WAN (wide area network), the Internet, or an Intranet, among others. The computer systems 82 and 90 may execute a program (or programs) in a distributed fashion. For example, computer 82 may execute a first portion of the program (or programs) and computer system 90 may execute a second portion of the program (or programs). As another example, computer 82 may display the graphical user interface of a program and computer system 90 may execute the functional code of the program.

In one embodiment, the graphical user interface of the program may be displayed on a display device of the computer system 82, and the functional code may execute on a device coupled to the computer system 82. The device may include a programmable hardware element and/or may include a processor and memory medium which may execute a real time operating system. In one embodiment, the program may be downloaded and executed on the device. For example, an application development environment with which the program is associated may provide support for downloading a program for execution on the device in a real time system.

Exemplary Systems

Embodiments of the present invention may be used in any technical domain in which machine vision is used. For example, embodiments may be involved with performing test and/or measurement functions; controlling and/or modeling instrumentation or industrial automation hardware; modeling and simulation functions, e.g., modeling or simulating a device or product being developed or tested, etc. Exemplary test applications where the program may be used include hardware-in-the-loop testing and rapid control prototyping, among others.

However, it is noted that the present invention can be used for or in relation to a plethora of applications and is not limited to the above applications. In other words, applications discussed in the present description are exemplary only, and the present invention may be used in any of various types of systems. Thus, the system and method of the present invention is operable to be used in any of various types of applications, including the control of other types of devices such as multimedia devices, video devices, audio devices, telephony devices, Internet devices, etc., as well as general purpose software applications such as word processing, spreadsheets, network control, network monitoring, financial applications, games, etc.

Figure 3A:
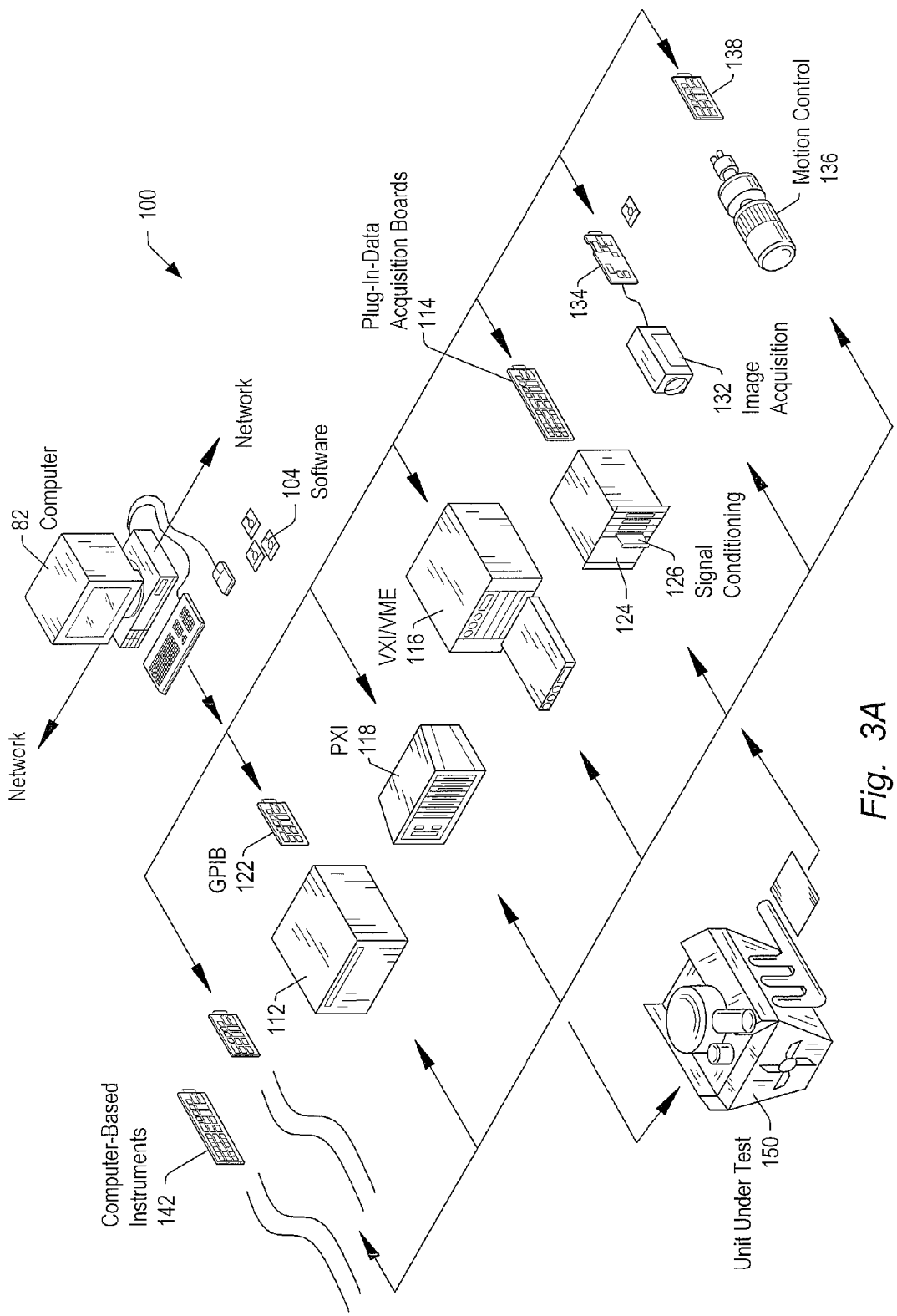
FIG. 3A illustrates an instrumentation control system according to one embodiment of the invention.

FIG. 3A illustrates an exemplary instrumentation control system 100 which may implement or use embodiments of the invention. The system 100 comprises a host computer 82 which couples to one or more instruments. The host computer 82 may comprise a CPU, a display screen, memory, and one or more input devices such as a mouse or keyboard as shown. The computer 82 may operate with the one or more instruments to analyze, measure, or control a unit under test (UUT)

or process 150, e.g., a product in a manufacturing process, particularly using a machine vision system.

The one or more instruments may include a GPIB instrument 112 and associated GPIB interface card 122, a data acquisition board 114 inserted into or otherwise coupled with chassis 124 with associated signal conditioning circuitry 126, a VXI instrument 116, a PXI instrument 118, a video device or camera 132 and associated image acquisition (or machine vision) card 134, a motion control device 136 and associated motion control interface card 138, and/or one or more computer based instrument cards 142, among other types of devices. The computer system may couple to and operate with one or more of these instruments. The instruments may be coupled to the unit under test (UUT) or process 150, or may be coupled to receive field signals, typically generated by transducers. The system 100 may be used in a data acquisition and control application, in a test and measurement application, an image processing or machine vision application, a process control application, a man-machine interface application, a simulation application, or a hardware-in-the-loop validation application, among others.

Figure 3B:
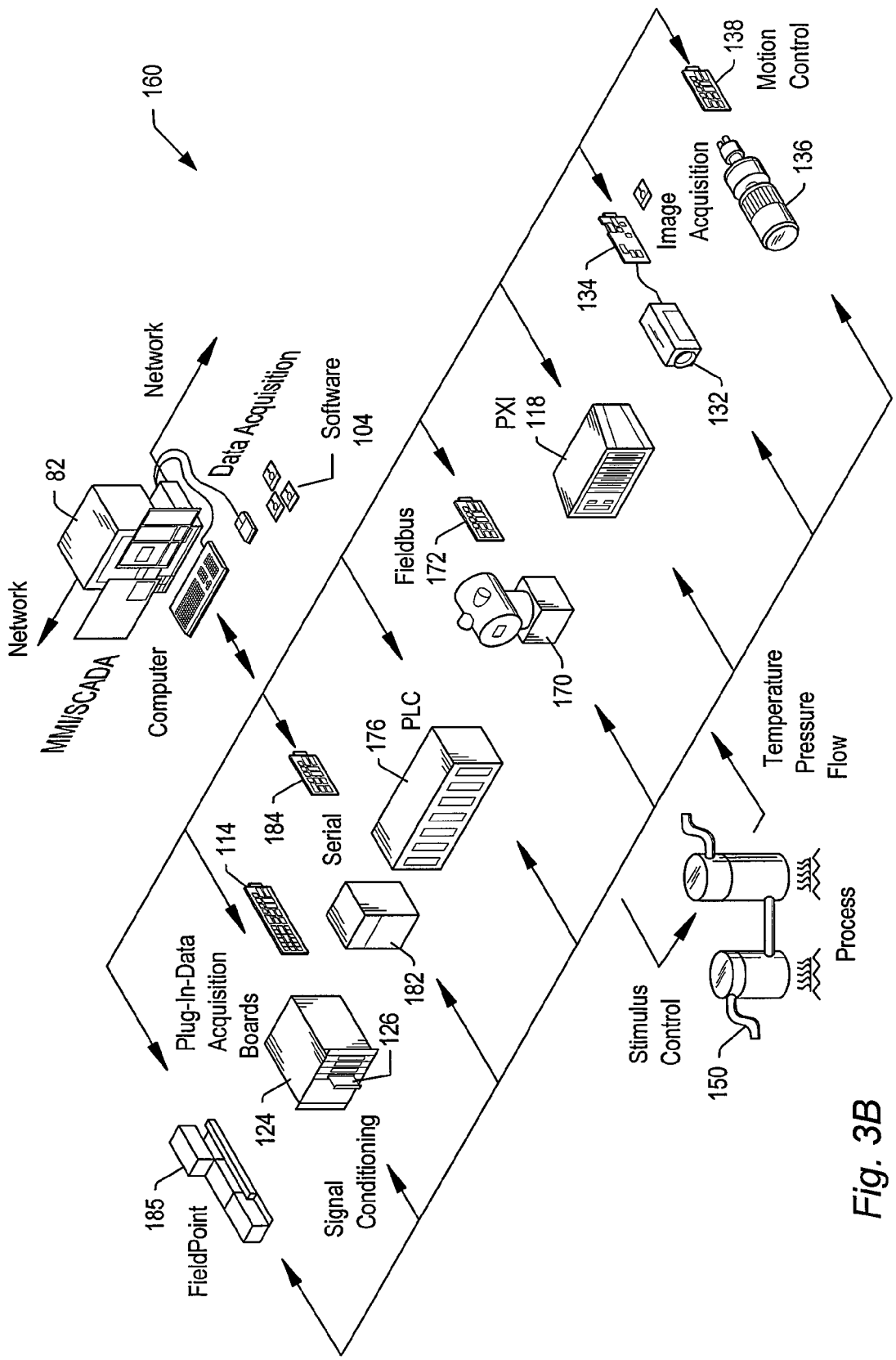
FIG. 3B illustrates an industrial automation system according to one embodiment of the invention.

FIG. 3B illustrates an exemplary industrial automation system 160 which may implement or use embodiments of the invention. The industrial automation system 160 is similar to the instrumentation or test and measurement system 100 shown in FIG. 3A. Elements which are similar or identical to elements in FIG. 3A have the same reference numerals for convenience. The system 160 may comprise a computer 82 which couples to one or more devices or instruments. The computer 82 may comprise a CPU, a display screen, memory, and one or more input devices such as a mouse or keyboard as shown. The computer 82 may operate with the one or more devices to perform an automation function with respect to a process or device 150, such as MMI (Man Machine Interface), SCADA (Supervisory Control and Data Acquisition), portable or distributed data acquisition, process control, advanced analysis, or other control, among others, using a machine vision system.

The one or more devices may include a data acquisition board 114 inserted into or otherwise coupled with chassis 124 with associated signal conditioning circuitry 126, a PXI instrument 118, a video device 132 and associated image acquisition card 134, a motion control device 136 and associated motion control interface card 138, a fieldbus device 170 and associated fieldbus interface card 172, a PLC (Programmable Logic Controller) 176, a serial instrument 182 and associated serial interface card 184, or a distributed data acquisition system, such as the Fieldpoint system available from National Instruments, among other types of devices.

Figure 4A:
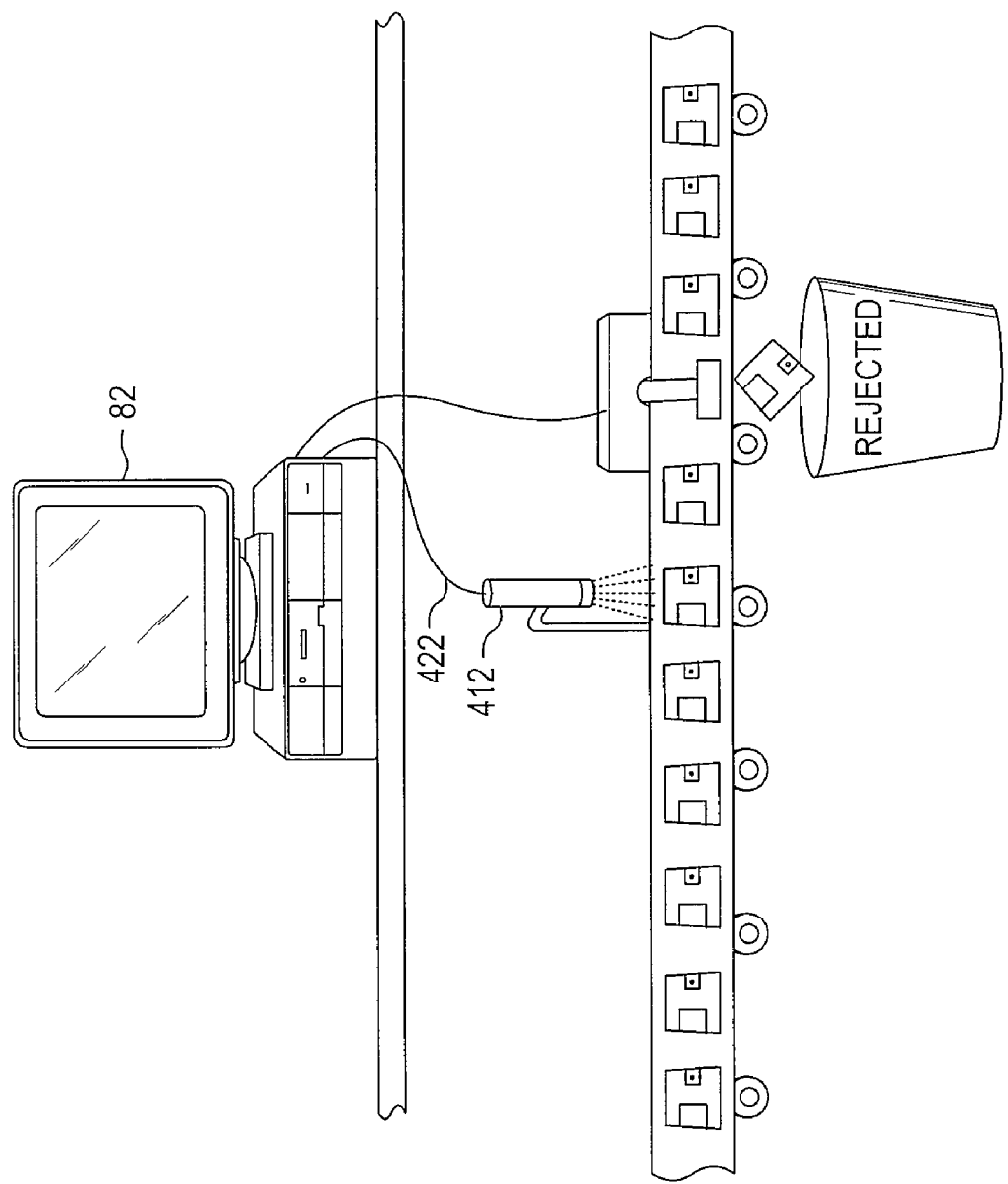
FIGS. 4A and 4B illustrate machine vision systems, according to embodiments of the present invention.
Figure 4B:
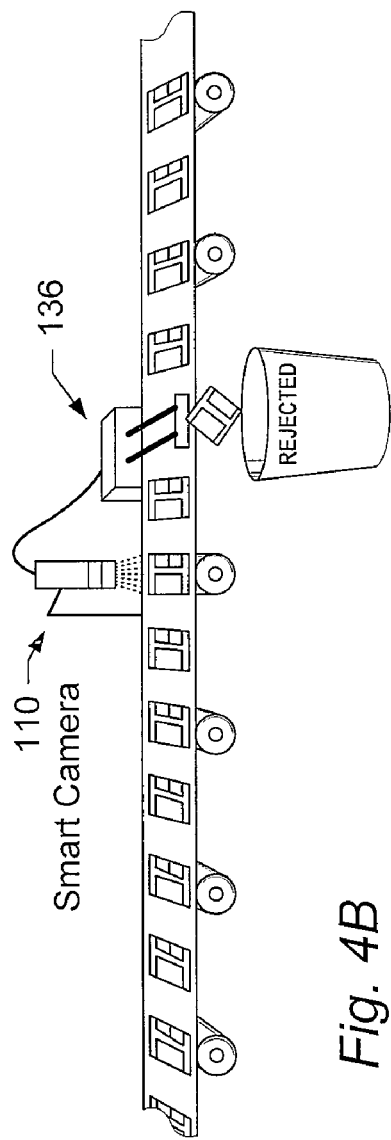

FIGS. 4A and 4B—Machine Vision Systems

FIGS. 4A and 4B illustrate exemplary vision systems, each including a vision system and a control device 13, e.g., examples of a machine vision application wherein embodiments of the present invention may be used. As may be seen in FIG. 4A, the machine vision system may include a host 82 and a video source 412, e.g., an analog or digital camera. The video source 412 preferably produces a digital video signal which includes an image or a sequence of images or video frames, or other data desired to be acquired. The digital video signal may be provided through a wire or cabling 422 to the host computer 82 for storage and/or processing. The host computer may include an image acquisition or frame grabber board (also called a video capture board). The host computer 82 preferably includes various standard components, such as at least one CPU, memory, etc. The host computer 82 may store a template image or pattern. In one embodiment, the host computer 82 may also store software which performs vision inspection, e.g., using pattern matching or other types of image analysis, e.g., to locate zero or more instances of the template image in the target image, the results of which may be used to characterize the vision system, as will be described in detail below. In the embodiment of FIG. 4A, the host computer 82 may receive the target image from the video source 412 and perform pattern matching using the stored template image. However, in other embodiments, the computer 82 may receive the target image and/or the template image from another source, or one or both of the target image and the template image may be pre-stored on the computer.

Thus, in the machine vision application of FIG. 4A, the computer system 82 is coupled to a camera 412 and operates to receive a target image and perform pattern matching to locate one or more instances of a template image in the target image. The computer system of FIG. 4A may be programmed according to one embodiment of the present invention to perform vision inspection on images that simulate various conditions of the vision system. The techniques of the present invention may be used in various types of machine vision applications. For example, the computer 82 may be embodied in various form factors and/or architectures, e.g., a robot, among others. It is also noted that the characterization techniques described herein may be performed in any of various manners, either in software, programmable logic, or hardware, or a combination thereof.

In the embodiment of FIG. 4B, the processor and memory are incorporated in a smart camera 110, i.e., where the smart camera includes the camera, the processor and memory, and a chassis, containing the camera and the processor and memory. In other embodiments, in addition to, or instead of, the processor, the smart camera may include a programmable hardware element, e.g., a field programmable gate array (FPGA), an application specific integrated circuit (ASIC), etc.

Similar to the embodiment of FIG. 4A, in this embodiment, the processor in the smart camera 110 may perform the desired image processing functions, including optionally performing an operation based on determined characteristics of the image, e.g., determining control data. Thus, in the embodiments of FIGS. 4A and 4B, the processor in the smart camera 110 or the computer system 82 may perform at least a portion of the methods and techniques described herein, and/ or may control the control device 136.

In the embodiments of FIGS. 3A, 3B, 4A and 4B, one or more of the various devices may couple to each other over a network, such as the Internet. In one embodiment, the user operates to select a target device from a plurality of possible target devices for programming or configuration using a program. Thus the user may create a program on a computer and use (execute) the program on that computer or deploy the program to a target device (for remote execution on the target device) that is remotely located from the computer and coupled to the computer through a network.

Figure 5:
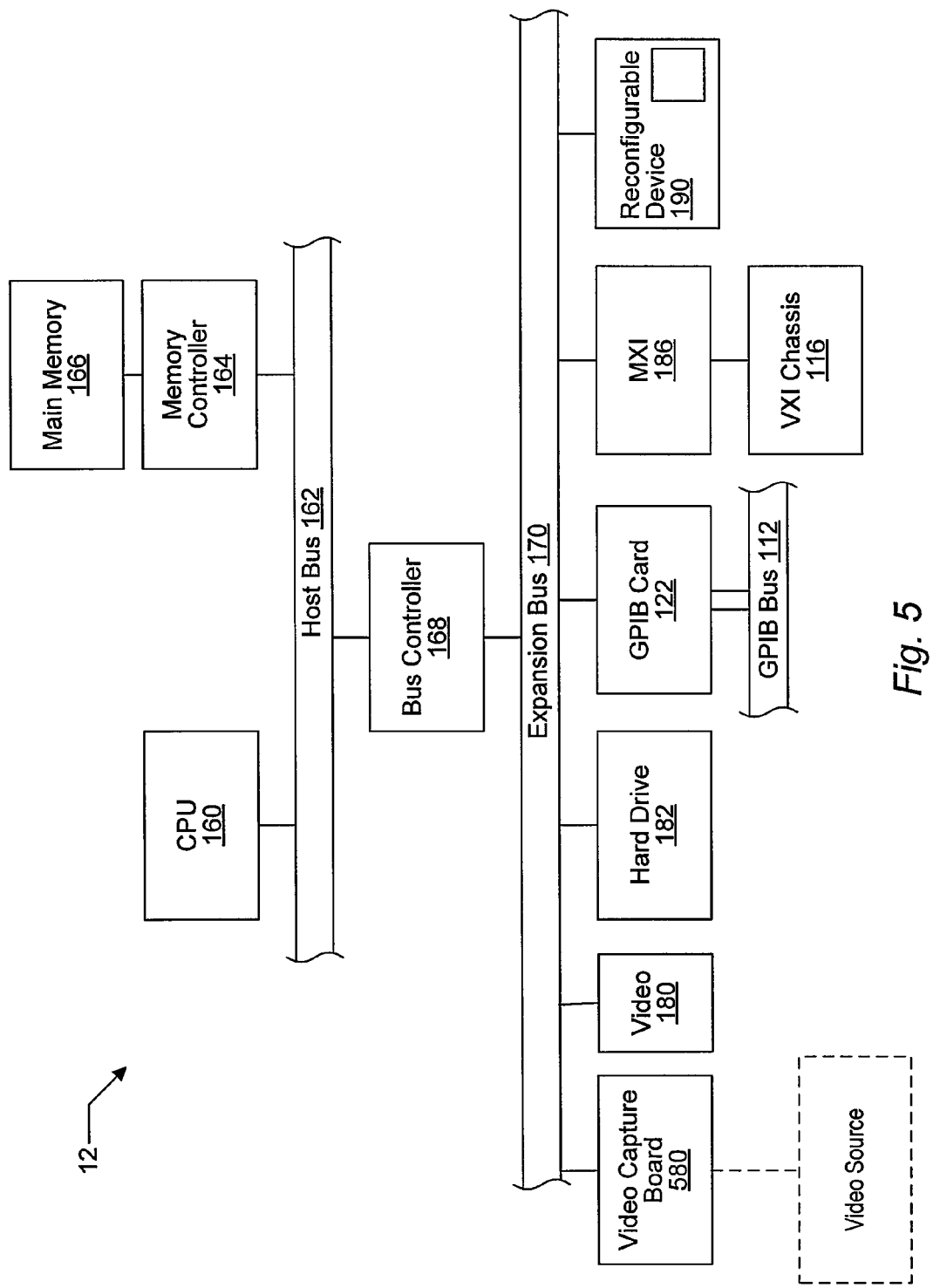
FIG. 5 is an exemplary block diagram of the computer systems of FIGS. 2A, 2B, 3A and 3B.

FIG. 5—Computer System Block Diagram

FIG. 5 is a block diagram representing one embodiment of the computer system 82 and/or 90 illustrated in FIGS. 2A and 2B, or computer system 82 shown in FIG. 3A or 3B. It is noted that any type of computer system configuration or architecture can be used as desired, and FIG. 5 illustrates a representative PC embodiment. It is also noted that the computer system may be a general purpose computer system, a computer implemented on a card installed in a chassis, or other types of embodiments. Elements of a computer not necessary to understand the present description have been omitted for simplicity.

The computer may include at least one central processing unit or CPU (processor) 160 which is coupled to a processor or host bus 162. The CPU 160 may be any of various types, including an x86 processor, e.g., a Pentium class, a PowerPC processor, a CPU from the SPARC family of RISC processors, as well as others. A memory medium, typically comprising RAM and referred to as main memory, 166 is coupled to the host bus 162 by means of memory controller 164. The main memory 166 may store program instructions executable to implement embodiments of the present invention, as well as images that may be used to characterize a vision system. The main memory may also store operating system software, as well as other software for operation of the computer system.

The host bus 162 may be coupled to an expansion or input/output bus 170 by means of a bus controller 168 or bus bridge logic. The expansion bus 170 may be the PCI (Peripheral Component Interconnect) expansion bus, although other bus types can be used. The expansion bus 170 includes slots for various devices such as described above. The computer 82 further comprises a video display subsystem 180 and hard drive 182 coupled to the expansion bus 170, as well as a video capture board 580 operable to capture images from a video source.

As shown, a device 190 may also be connected to the computer. The device 190 may include a processor and memory which may execute a real time operating system. The device 190 may also or instead comprise a programmable hardware element. The computer system may be operable to deploy a program to the device 190 for execution of the program on the device 190. The deployed program may take the form of program instructions or data structures that directly represents the program. In some embodiments, the program may be or include a graphical program. Alternatively, the deployed graphical program may take the form of text code (e.g., C code) generated from the graphical program. As another example, the deployed graphical program may take the form of compiled code generated from either the graphical program or from text code that in turn was generated from the graphical program. One exemplary type of graphical program is that created using the LabVIEW graphical programming environment, provided by National Instruments Corporation. Graphical software programs which perform data acquisition, analysis and/or presentation, e.g., for measurement, instrumentation control, industrial automation, modeling, or simulation, such as in the applications shown in FIGS. 3A and 3B, may be referred to as virtual instruments.

As discussed above, it is difficult for a vision system integrator to physically mimic all the variations that can take place on the production line. One way to alleviate this problem is to give machine vision system developers the ability to model their vision system in software and use this model to simulate different imaging conditions. For example consider a machine vision system that is being designed to read 2D barcodes. After the camera and optics have been set up, the designer of the system will acquire an image and then setup the parameters of the machine vision software to locate and read the barcode. With the simulation tools, he or she can then generate variations of the image that may be possible in the production line, and test and fine tune the barcode reader to work under all these conditions. This process may be used to improve the reliability of the machine vision system.

Thus, the computer may also store application code, specifically, simulation software (and/or hardware), e.g., for simulating the vision system and/or conditions of and for the vision system. Examples of imaging conditions that may be simulated include, but are not limited to: perspective, scale, rotation, offset, brightness, contrast, gamma, focus blur, motion blur, and noise. The user may provide a value range for each desired condition and then the application may generate images based on a sample set of possible combinations of these values. The generated images may be embedded with the parameter values that were used to create them and deposited into a designated output directory. These images can then be used to test the robustness of the user's vision solution.

The application (or applications) may thus include various functions or controls to simulate machine vision system conditions. The following describes controls that may be included in the application(s), although it should be noted that the controls or functions described are meant to be exemplary only.

Perspective

The purpose of the perspective control is to model the effect of changing the camera's position. The user may generate images from different viewpoints by either rotating the (simulated) camera, panning the camera, altering the position of the camera itself, or altering the point the camera is looking at. The final perspective image may be generated by rendering a scene with the 3D picture controls. A rectangle may be created and then textured with the original image. The default position of the camera may assume that the camera is orthogonal to the original image, looking at the image's center, and that the image occupies the entire field of view. Additionally, this control may require the user to supply a scaling constant so that the real world coordinates of the camera's position can be translated into the appropriate internal representation.

Geometric

The geometric control may simulate affine changes in the object being imaged, specifically, changes in scale, rotation, and offset. In some embodiments, these functions may be implemented using existing programs or routines (e.g., VIs) in the vision system software, e.g., in a vision module.

Intensity

The intensity control may model simple changes in lighting conditions, e.g., by adjusting the brightness, contrast, and gamma of the image. These functions may also be implemented using existing programs or VI's in the vision system software or module.

Focus Blur

The focus blur control may simulate the blurring that occurs when an image is out of focus. To model this correctly, the user may provide detailed information about the camera being used. The specific parameters needed may include: focal length, f-stop, camera resolution (pixels), CCD size (mm), distance of the camera from the imaging plane when in focus, and the shape and orientation of the camera's shutter. The effect may be created by first calculating the size of the circle of confusion on the camera's imaging sensor. This value along with the shutter's shape may determine the size and shape of the convolution kernel used to generate the final blur. It should be noted that the focus blur may assume that a planar scene is being imaged. For non planar scenes, a grayscale depth map may be provided.

Motion Blur

Camera motion during the image acquisition process can generate a motion blur. This effect may be modeled by creating a convolution kernel that consists of a single pixel width line oriented in the direction of the camera motion. The length of the line determines the amount of the blur. The value of each of the kernel elements is the inverse of the length of the line.

Noise

Image noise can come from a variety of different sources. This effect may be modeled by allowing the user to choose from three different types of noise: Uniform, Gaussian, and Impulse. The user may control the amount of noise added to the image and the standard deviation (Gaussian) or range (Uniform) of the values. In some embodiments, the location of the noisy pixels may be determined via a low discrepancy 2D Halton sequence, thus ensuring a relatively uniform spatial distribution across the image.

Of course, combinations of any of the above may also be important, as there may be synergistic effects between the individual conditions. Embodiments of a method for using this simulation approach to characterize vision systems are discussed below.

Figure 6:
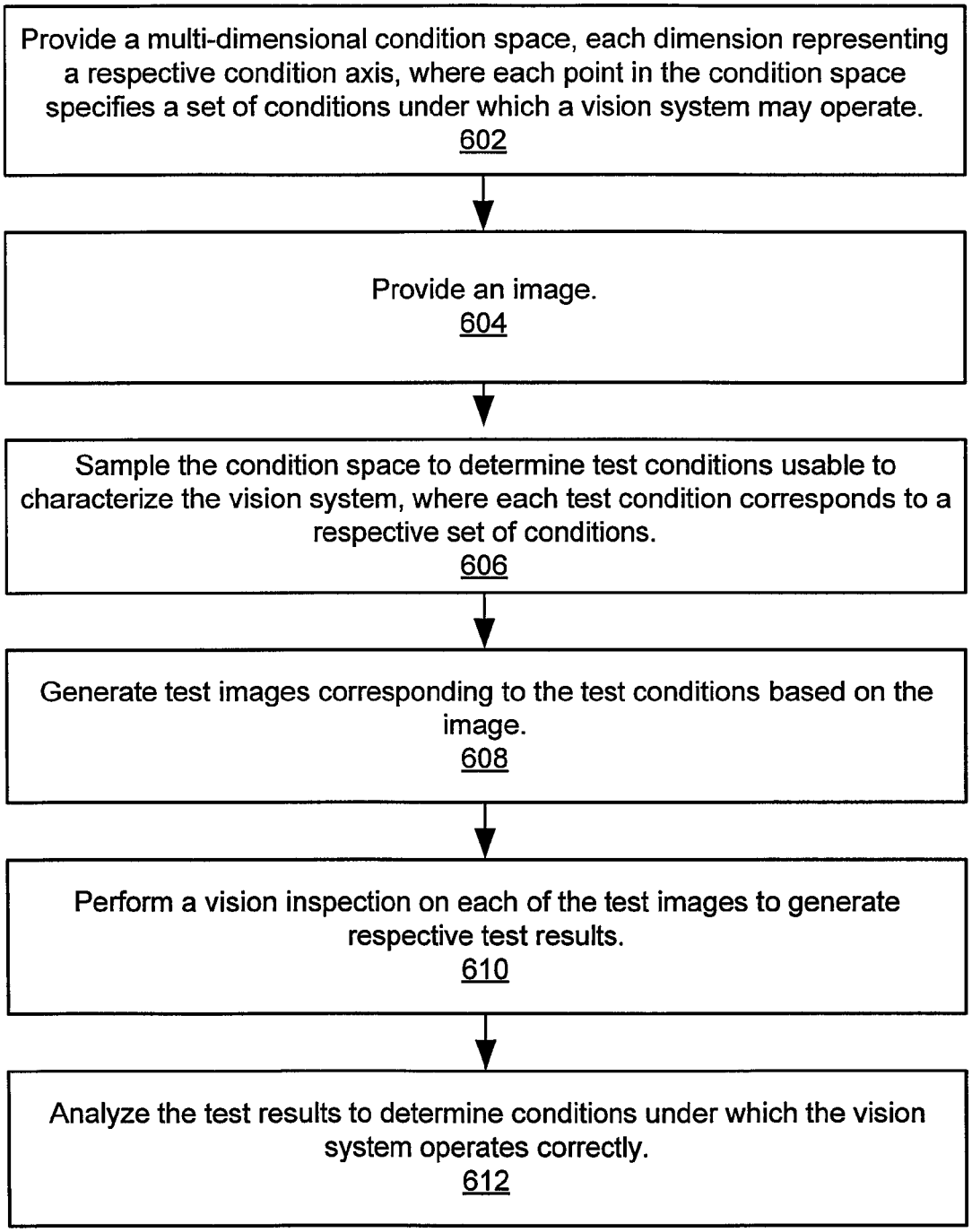
FIG. 6 is a flowchart diagram illustrating one embodiment of a method for characterizing a vision system.

FIG. 6—Method for Characterizing a Vision System

FIG. 6 illustrates a method for characterizing a vision system, according to one embodiment. The method shown in FIG. 6 may be used in conjunction with any of the computer systems or devices shown in the above Figures, among other devices. In various embodiments, some of the method elements shown may be performed concurrently, in a different order than shown, or may be omitted. Additional method elements may also be performed as desired. As shown, this method may operate as follows.

Figure 7A:
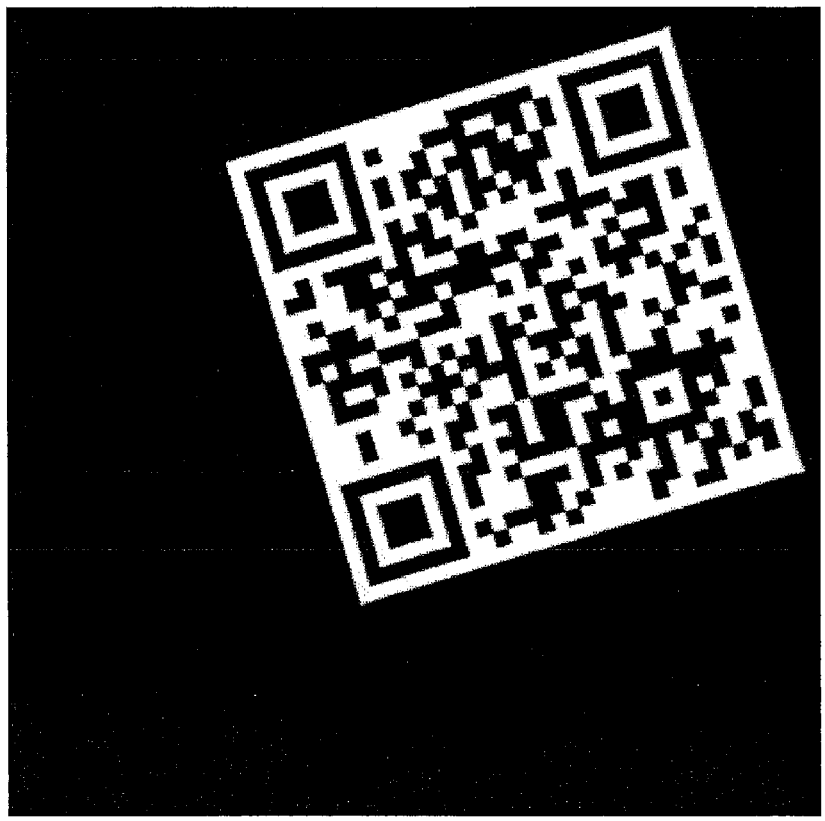
FIGS. 7A-7F illustrates exemplary effects of inspection conditions on an image, according to one embodiment.
Figure 7B:
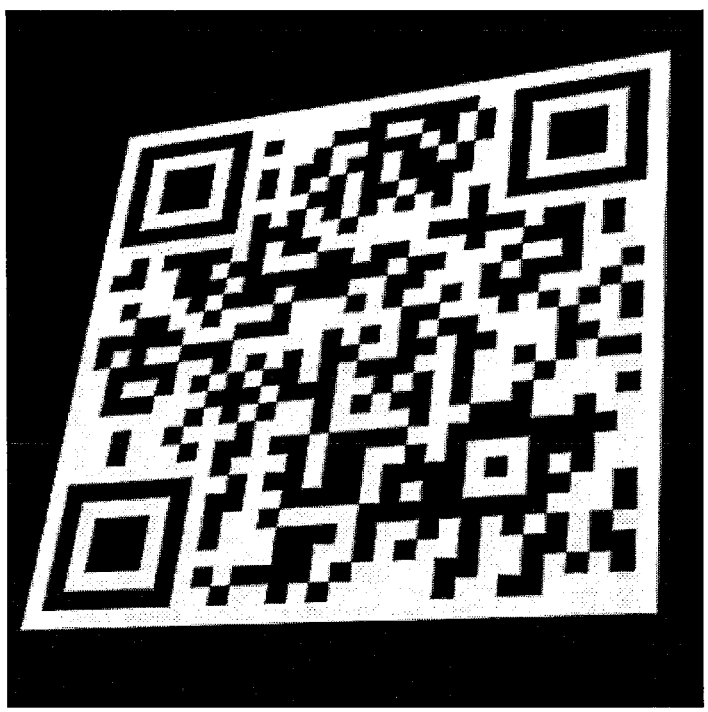

In 602, a condition space may be provided, where the condition space includes a plurality of dimensions, each dimension representing a respective condition axis, and where each point in the condition space specifies set of conditions under which a vision system may operate. For example, the condition axes may include, but are not limited to, axes related to image object geometry, camera geometry, lighting, focus blur, motion blur, and/or noise. For example, condition axes related to image object geometry may include axes for one or more of: object scale, object rotation, or object offset, among others. FIG. 7A illustrates the effects of these conditions, where, as may be seen, an image object, e.g., image of a 2D bar code, is shown scaled (e.g., diminished), rotated (e.g., ~20 degrees CCW), and offset (e.g., upward and rightward). Exemplary condition axes related to camera geometry may include axes for one or more of: camera position, look at position, camera pan, or camera rotation, among others. FIG. 7B illustrates exemplary effects due to these conditions. Note that the effects of camera geometry may be quite similar to those of image object geometry, although the causes and remedies are distinctly different-specifically, camera movement, position, and orientation, versus those of the object being inspected.

Figure 7C:
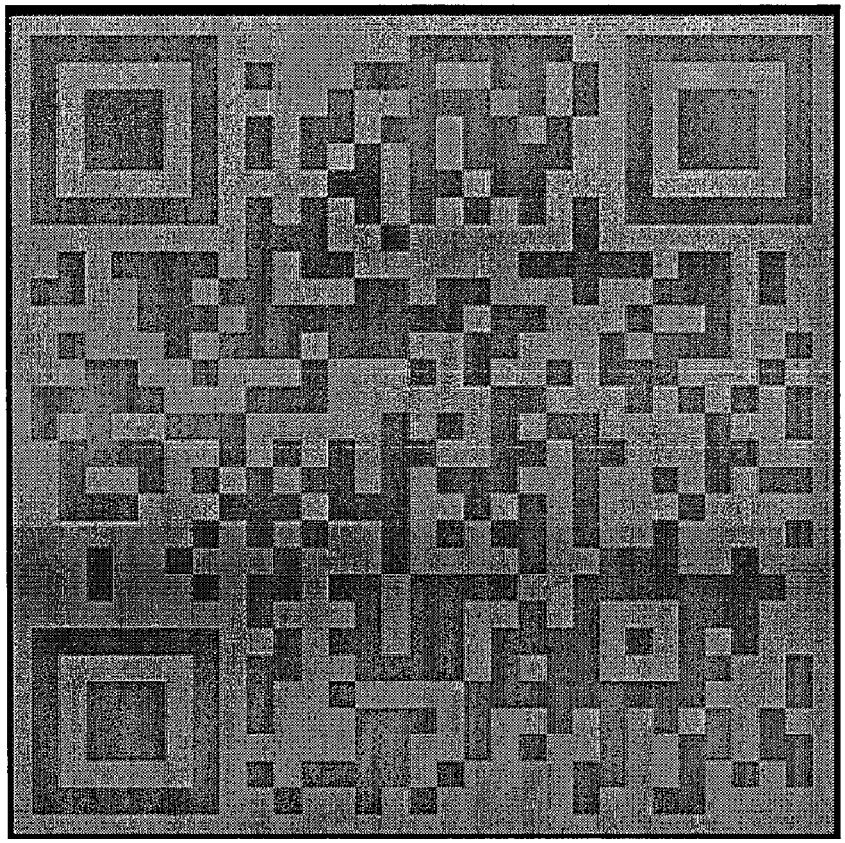
Figure 7D:

Exemplary condition axes related to lighting may include axes for one or more of brightness, contrast, or gamma, among others. FIG. 7C illustrates exemplary effects due to these conditions, as are well known to those of skill in the art. FIG. 7D illustrates focus blur, due to discrepancies between the focal length of the camera and the distance to the image object.

Figure 7E:
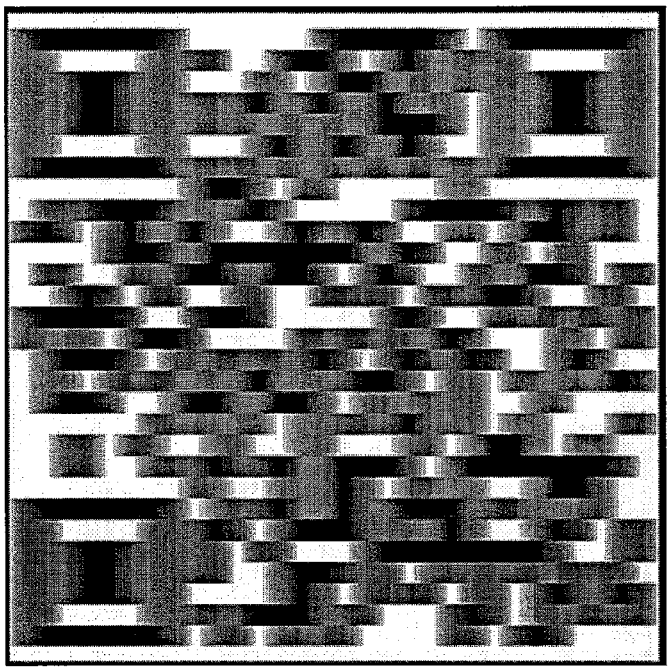
Figure 7E:
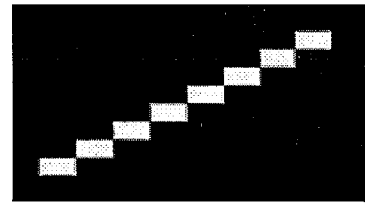

Exemplary condition axes related to motion blur may include axes for length of blur and/or angle of blur. As is well known, motion blur is generated by movement during exposure, e.g., during the creation of the image. FIG. 7E illustrates exemplary effects due to such motion.

Figure 7F:
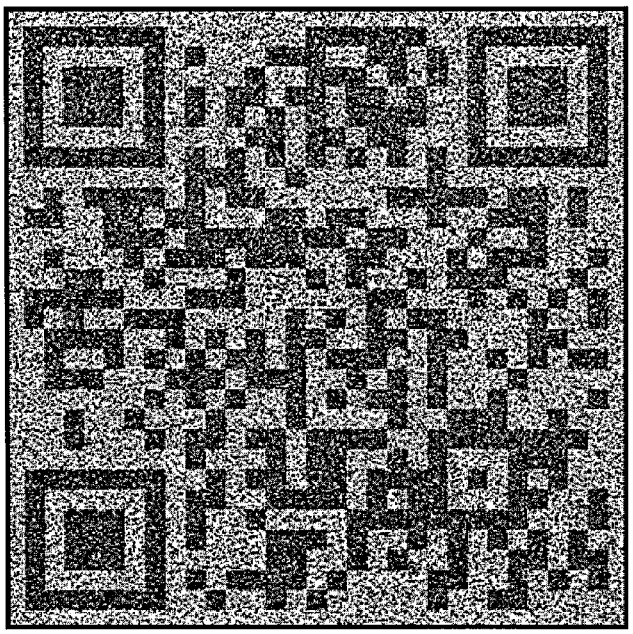

Exemplary condition axes related to noise may include axes for one or more of: noise type, e.g., uniform, Gaussian, and/or impulse (i.e., "salt and papper"), standard deviation, or amount of noise, among others, as illustrated by FIG. 7F.

It should be noted that the conditions and effects described are meant to be exemplary only, and that other conditions and effects may be accommodated as desired.

In preferred embodiments, a graphical user interface (GUI) may be provided whereby the condition space may be specified. For example, the GUI may allow a user to configure bounds for condition axes to limit the size of the searchable space, sampling schemes, e.g., number of samples, sampling algorithm, and so forth.

Figure 8:
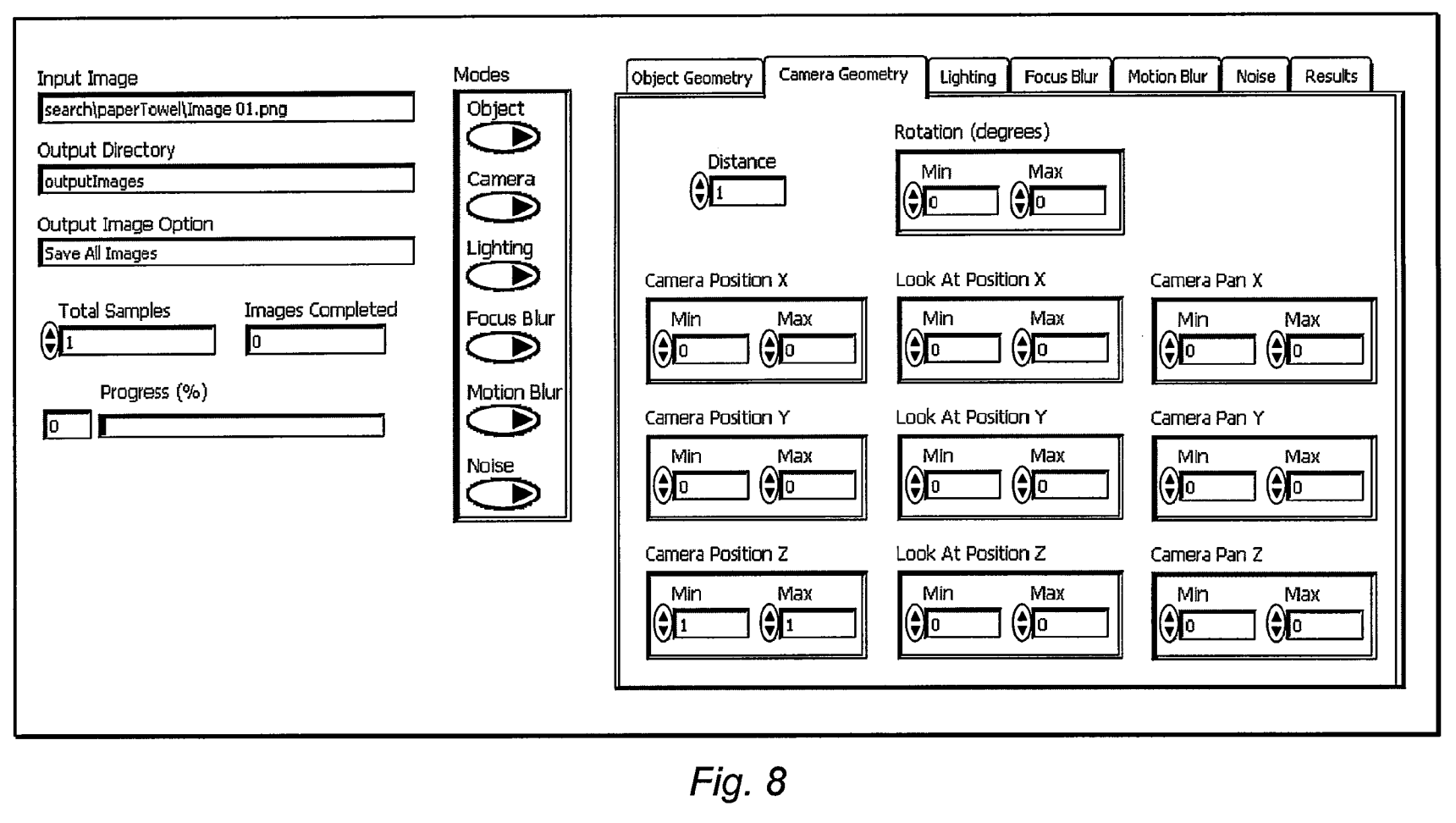

FIG. 8 illustrates an exemplary GUI for specifying or configuring a condition space, according to one embodiment. As may be seen, this exemplary GUI allows a user to specify which condition axes to include in the condition space, as well as ranges, i.e., upper and lower bounds, for each axis. In this particular embodiment, the axes may be selected via respective buttons in a "Modes" section of the GUI, and axis bounds specified via tabbed sections with parameter value entry fields. Note that in some embodiments, default values may be provided as desired, e.g., defining a default condition space. As FIG. 8 shows, this GUI also allows the user to specify an input image, an output directory to which results may be stored, output image options, number of samples, and progress indicators, although other GUI elements may be included as desired. Note that the tabbed sections include a "Results" tab, whereby results may be displayed.

Note that these condition bounds or ranges may be considered to be tolerance specifications for a vision system, where, for example, it is desired to determine what tolerances are required that result in robust operation of the vision system.

Thus, in some embodiments, a GUI may be used to specify simulation of different imaging effects. For example, the user may input an inspection image (such as the image of a 2D barcode is to be located and read) and then select the types of effects he or she wants applied on the image. As indicated above, imaging effects may include changes in the location of the barcode in the image, changes in the focus of the lens, perturbations in the image due to vibration (motion) of the camera, etc. For each imaging effect, the user may specify the range within which the parameters of the imaging effect can vary. For example in the Camera Geometry effect settings, the user may specify that the camera may rotate between −10 and 10 degrees during the inspection. The application may then be operable to generate a series of output images that are obtained by applying all the imaging effects to the original input image, as will be discussed in more detail below.

In 604, an image may be provided. This image is preferably representative of real-world images/image-objects to which the vision system being characterized will be applied, e.g., an image of a circuit board produced in a manufacturing plant that will utilize the vision system, a human face to be automatically recognized, etc. As described above, in one embodiment, a GUI such as that of FIG. 8, may be used to specify this image.

In 606, the condition space may be sampled. There are a variety of sampling schemes that may be used to sample the condition space, where the particular scheme used may be selected based on attributes of the condition space or more generally, on the nature of the object being inspected or resource limitations, e.g., disk space, CPU, etc. For example, in one embodiment, the condition space may be of three or more dimensions, and any sampling scheme of the condition space may be used as desired, e.g., uniform sampling, random sampling, pseudo-random sampling, sampling according to a low discrepancy sequence, e.g., a Halton sequence, and so forth, as desired. In another exemplary embodiment, the condition space may be of two or more dimensions, and a sampling scheme based on a pseudo-random sequence, e.g., a low discrepancy sequence may be used, although it should be noted that in other embodiments, any sampling scheme may be used as desired.

There are a number of benefits to utilizing a deterministic pseudo-random sampling scheme such as low discrepancy sequences, e.g., a Halton sequence, e.g., the sequences, although quasi-random, are deterministic, and thus repeatable. Additionally, such sequences may generate nearly uniform distributions, and may do so at any of a variety of scales and sample points.

Figure 9:
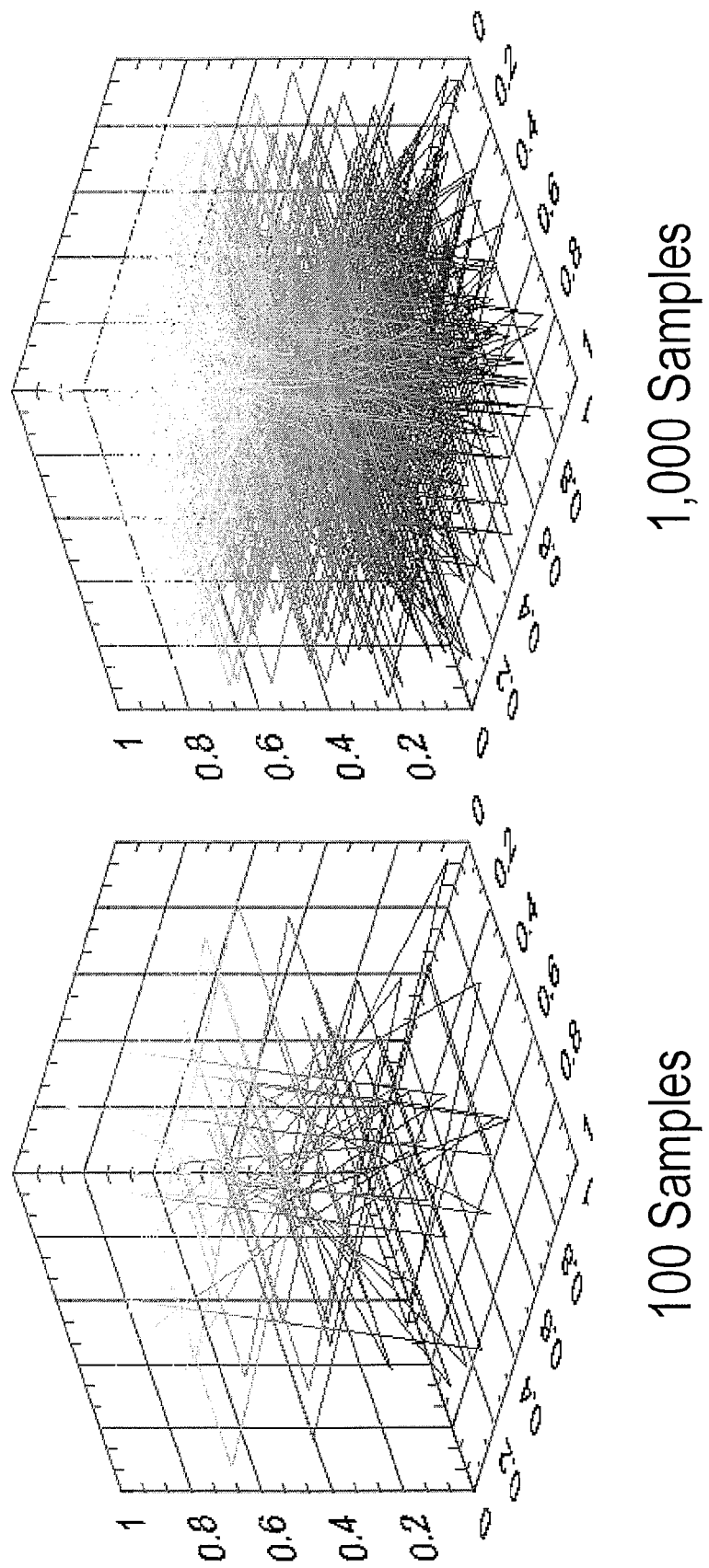
FIG. 9 illustrates exemplary Halton sequences in three dimensional spaces, according to one embodiment.

FIG. 9 illustrates an exemplary three dimensional (3D) space sampled according to a Halton sequence at various resolutions, specifically, with 100 samples (left), and with 1,000 samples (right). As those of skill in the art are aware, a properly specified Halton sequence (e.g., in this (3D) case based on a triplet of prime numbers, and possibly discarding some initial set of points) may provide a reliable means to sample a large space in a nearly uniform manner, and may facilitate such sampling for virtually any number of points. Of course, in other embodiments, other low discrepancy sequences may be used as desired, e.g., per Faure, Hammersley, Sobol, Niederreiter, van der Corput, etc.

Thus, in preferred embodiments, the condition space may be sampled according to a low discrepancy sequence to determine a plurality of test conditions usable to characterize the vision system, where each test condition corresponds to a respective set of conditions. In other words, each test condition includes parameter values for each axis of the condition space, and may thus define a set of conditions under which the vision system may inspect an image or image object.

In 608, a plurality of test images corresponding to the plurality of test conditions may be generated based on the image. Said another way, each test condition may be used to generate a respective test image that reflects the effects of the test condition (see, e.g., FIGS. 7A-7F) on the original image (of 604).

Figure 10:
FIG. 10 illustrates exemplary test images generated according to a Halton sequence in condition space, according to one embodiment.

FIG. 10 is an exemplary illustration of test images generated according to sampled points of the condition space, and arranged to correspond to or reflect the sample points. More specifically, these test images were generated according to the Halton sequence-based sampling of FIG. 9. As may be seen, each test image suffers from some complication due to the corresponding conditions specified by the sample point for that image. Thus, the plurality of test images may provide a broad spectrum of vision inspection problems that may be used to characterize performance of a vision system.

In some embodiments, one or more of the test conditions may be implemented by modifying the vision system, e.g., by moving the camera and/or target, changing the focus of the camera lens, changing the lighting, and so forth. However, note that in general, it would not be practical or efficient to generate all the test images by actually modifying a vision system per the sample point conditions. Thus, in preferred embodiments, generating a plurality of test images corresponding to the plurality of test conditions based on the image may include generating the plurality of test images by applying image processing functions to the image that simulate the plurality of test conditions. Thus, the above-mentioned conditions may be simulated and applied to the original image to produce effects that degrade the quality of the image, thus generating the test images.

Thus, referring again to FIG. 8, in some embodiments, generating a plurality of test images corresponding to the plurality of test conditions based on the image may include receiving user input to a graphical user interface specifying one or more of: test conditions to simulate, number of samples of the condition space to use, and/or range values for one or more of the condition axes. Then, based on the user input, image processing functions may be applied to the image that result in the appropriate effect. For example, to simulate focus blur, the method may simulate or model changes in camera distance, and, e.g., using optics equations, determine and apply blurring to the image due to camera distances that are not commensurate with the camera's focal length. Of course, this is but one example of a simulation technique for producing image effects due to conditions. Note that the simulations may make certain assumptions regarding the system and/or the image or image object. For example, with respect to focus blur, the method may assume a planar imaging surface (i.e., a flat object). If non-planar imaging surfaces are to be accommodated, other techniques may be used, e.g., for non-planar cases, a depth map may be used to simulate the condition effects.

In 610, a vision inspection may be performed on each of the plurality of test images to generate respective test results. In other words, the vision system to be characterized may perform vision inspections on the test images and generate results, e.g., indicating whether the inspection passed or failed.

In some embodiments, the sampling and the vision inspections may be performed conjunctively. For example, in some embodiments, the sampling the condition space, generating the plurality of test images, and performing a vision inspection on each of the plurality of test images may include: for each of a plurality of iterations: a) sampling the condition space to generate a condition point, b) generating a test image based on the condition point, c) performing a vision inspection on the test image, d) if the vision inspection fails, performing a)-c) for one or more condition points in a specified neighborhood of the condition point to determine a point for which the vision inspection passes. In other words, if an inspection fails for a particular set of conditions, the method may "search" some neighborhood of the point to determine if there are conditions nearby under which the inspection would pass, thereby determining part of a boundary between "passing" conditions and "failing" conditions. Thus, in some embodiments, based on the inspection results for a condition (point in the condition space), further testing may be performed in the neighbor of that condition/point to more precisely determine the boundary between a region of robustness and a region where inspection results may be unreliable.

In addition to, or instead of, the above, in some embodiments, the sampling the condition space, generating the plurality of test images, and performing a vision inspection on each of the plurality of test images may include: for each of a plurality of iterations: a) sampling the condition space to generate a condition point, b) generating a test image based on the condition point, c) performing a vision inspection on the test image, d) if the vision inspection fails, modifying parameters of the vision inspection (which may include modifying parameters of the vision system itself) and performing a)-c) in an iterative manner until the vision inspection passes. In other words, for each sampled point, when a failure occurs, the method may change the parameters that specify the conditions and/or the vision system, to determine if there are conditions nearby under which the inspection would pass. Thus, in some embodiments, the vision system/vision inspection may be "tuned" or otherwise modified, e.g., incrementally, to determine the boundaries of robust operation.

Finally, the test results may be analyzed to determine analysis results, specifically, conditions under which the vision inspection operates correctly. For example, the test results may be plotted or otherwise characterized to indicate the regions of the condition space that represent conditions under which the vision system (the vision inspection) operates correctly, i.e., passes images that should pass (and/or conversely, fails images that should fail), operates robustly. In one embodiment, the analyzing may include determining the fraction of passes of the vision inspection within the condition space, e.g., determining that 85% of the specified condition space results in correct inspections by the vision system, e.g., the vision system passes images that should pass under 85% of the specified conditions. As a more sophisticated example, in one embodiment, the analyzing may include determining a largest convex hull in the condition space specifying conditions under which the vision system is robust, i.e., under which vision inspections by the vision system will pass within a specified tolerance, e.g., where the vision system will correctly pass 98% of "matching" images or objects. Note, however, that any other type of analysis may be performed as desired, the above examples being exemplary only. Thus, the test results may be analyzed to characterize the vision system, i.e., to determine under what conditions the vision system may be expected to operate in a robust manner, meaning that images that should pass will pass, and those that shouldn't will not, at least to within some specified error or tolerance.

Once the test results have been analyzed, and the conditions under which the vision inspection operates correctly determined, the analysis results (the "pass" conditions) may be stored and/or output to a display. For example, in one embodiment, the maximal convex hull may be presented graphically, e.g., in the case where the condition space has high dimensionality, as one or more projections of a high-dimensional convex hull. As other examples, the analysis results may be represented in tabular fashion, as a collection of ranges, etc., as desired.

In one embodiment, the analysis results may be used to tune the vision system, e.g., the various physical parameters of the vision system may be adjusted or even reengineered to decrease tolerance levels of the various parameters to fall within the determined passing conditions. For example, if the camera's rotational freedom exceeds the angular conditions under which the inspection process is robust, the camera's motion control platform may be modified or configured to avoid operating outside the specified bounds for that parameter.

Figure 11:
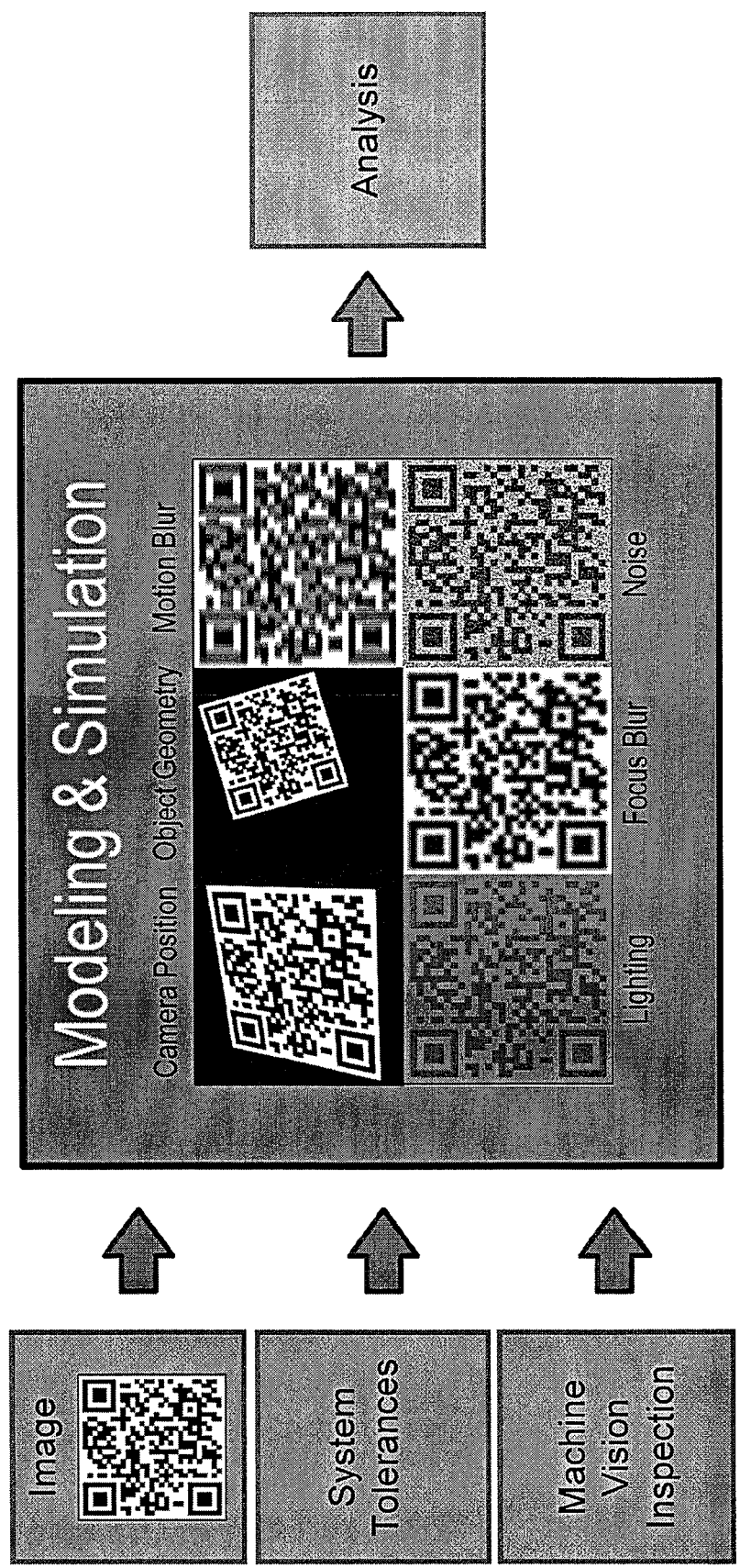
FIG. 11 illustrates primary inputs and output of the present invention, according to one embodiment.

FIG. 11 is a high-level illustration of the above process, indicating the use of machine vision simulations along with actual operation of the vision system and analysis of inspection results to characterize the vision system. As FIG. 11 shows, inputs to the process include the original image (of 604), system tolerances, which refer to the bounds of the condition space, and the machine vision inspection process itself. The modeling and simulation process generates the test images upon which the machine vision inspection is applied, which then produces test results which are input to an analysis process (and analyzed), as shown.

Thus, the robustness and reliability of a machine vision system may be determined based on simulated vision system conditions, and their effects on a template image. Said another way, once a series of images has been generated, the user can then run the machine vision inspection on each of the simulated images and use the results to analyze the robustness of the machine vision system. In determining robustness, the user is interested in determining how much variation in the image the machine vision inspection can tolerate and still operate correctly. Alternatively, the user may wish to determine the settings of the parameters for each imaging effect beyond which the machine vision inspection will fail (for an image that should pass).

Thus, summarizing the above, embodiments of the invention may provide an intelligent method to search a multidimensional space of image variations to find the region in this multidimensional space within which the machine vision system will work robustly, i.e., where variations in the imaging conditions will not affect the inspection results. Instead of creating all possible images in the multidimensional space, a random or quasi-random (e.g., Halton) sampling technique is used to sample the multidimensional image space. Moreover, in some embodiments, the search is directed, where at each step of the search, a (e.g., Halton) point is determined and the image corresponding to the parameters at that point in generated. The machine vision inspection may then be run on the generated image. If the inspection passes then another point may be determined and the process repeated. If the inspection fails, then points near the failed point may be analyzed (and processed as described above) to determine the point at which the inspection passes. The results of this search process may yield two types of results:

1) The user may get an idea of the percentage of passes to failures of the machine vision inspection within a given multidimensional space. This metric can be used to compare different methods to a machine vision inspection—for example if a particular machine vision inspection can be done using a pattern matching algorithm or an edge detection algorithm. The user can run both the methods on the simulated images in the multidimensional space and use the percentage of passes to failures to determine which of the two methods is more reliable (robust).

2) The user may get an idea of the tolerance of the machine vision inspection to variations in the imaging conditions. This information can be used to specify guidelines (tolerances) that need to be followed when duplicating the machine vision inspection on the production line.

Moreover, in some embodiments, the analysis may determine the largest convex region in the multidimensional space within which the machine vision inspection will always pass (within some tolerance or error). Additionally, in some embodiments, the failure points may be used to automatically improve the machine vision inspection step. For example, when the inspection fails, the parameters of the inspection step can be modified until it passes.

Example Case

The following presents an exemplary simple case according to one embodiment, where the above method is applied to line detection. In this example, the machine vision inspection involves the detection of the perforation line in a paper towel using an edge detection algorithm. In this particular application, the imaging assumes that the power towel under inspection can undergo some rotation; there may be some motion blur and the presence of noise in the image.

Figure 12:
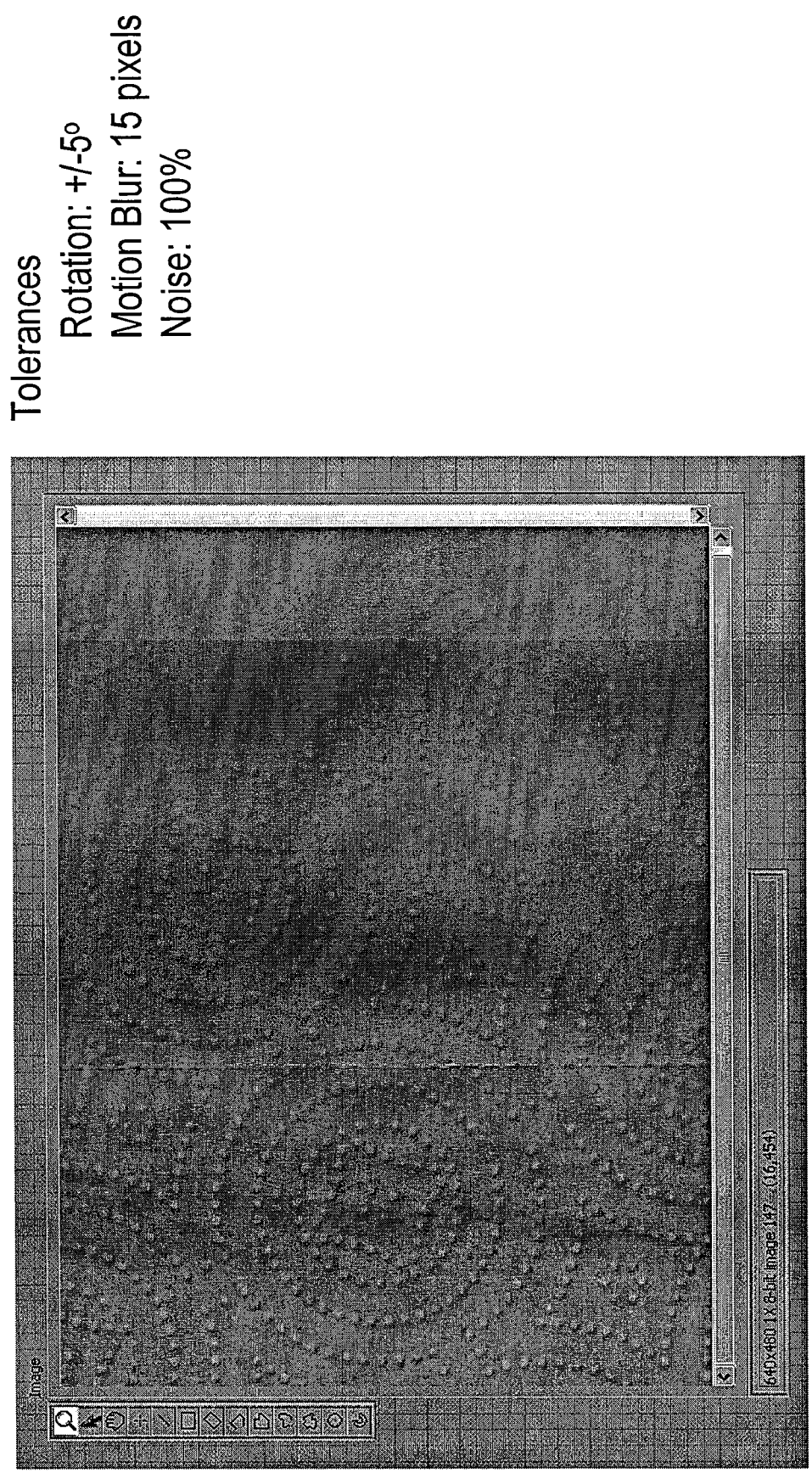
FIG. 12 illustrates an exemplary image suitable for characterizing a machine vision system, and initial ranges for the condition space, according to one embodiment.

FIG. 12 illustrates an image of the paper towel, where, as indicated above, the inspection process is to determine the perforation, which in this case is a vertical line. As FIG. 12 shows, the conditions or tolerances under which this image was "taken", or, more accurately, simulated, are +/−5 degrees rotation, motion blur of 15 pixels, and 100% noise. In other words, the condition space spans rotation from −5 degrees to +5 degrees, motion blur from 0 to 15 pixels, and noise levels from 0 to 100%. Note that in this simple example, the condition space is only three dimensional, although much higher dimensional spaces may be typical.

Figure 13:
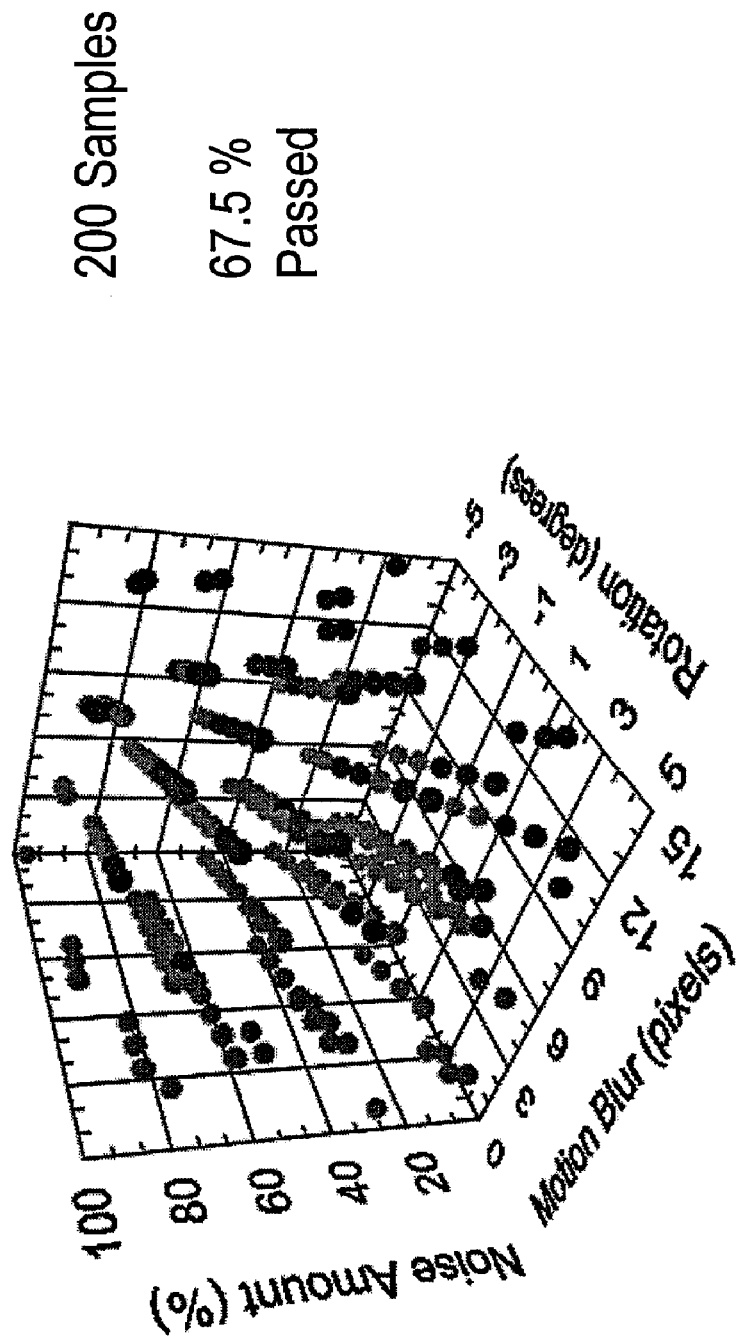
FIG. 13 illustrates inspection test results for the image and ranges of FIG. 12, according to one embodiment.

FIG. 13 illustrates exemplary pass/fail results from visual inspection based on sampling the space as specified in FIG. 12, where 200 points were sampled to determine 200 corresponding condition sets from the 3D search space, which in turn were used to generate 200 corresponding test images. In this figure, passes are indicated by white circles, and fails are indicated by solid black circles. As indicated, analysis of these test results determines that of the 200 samples (condition sets), 67.5% resulted in passes. Thus, the vision system was robust over 67.5% of the condition space.

Figure 14:
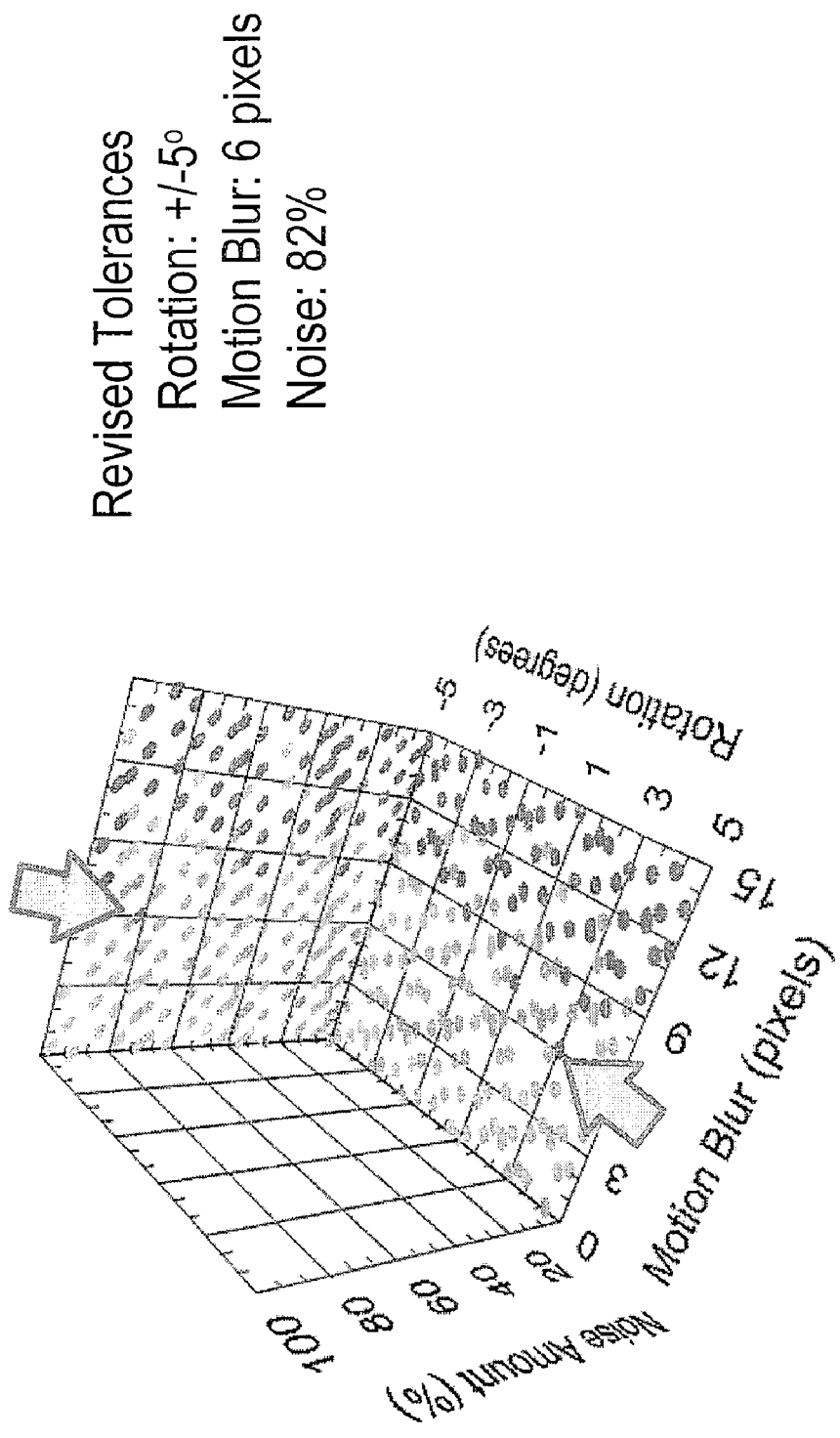
FIG. 14 illustrates inspection test results for the image and ranges of FIG. 12, with an identification of revised tolerances for the vision system within which inspections are robust, according to one embodiment.

As indicated above, these analysis results may be used to refine the vision system, e.g., reducing the tolerance of the system to minimize or even eliminate improper failures in the inspection process. FIG. 14 illustrates exemplary results from visual inspection based on sampling a similar space as that of FIG. 12, but at a higher sampling rate (higher numbers of samples), where ranges values or parameter bounds are identified (see arrows) within which the vision inspection is robust, specifically, tolerances of +/−5 degrees rotation (unchanged), motion blur of 0-6 pixels, and 0-82% noise, i.e., inspection within the condition space portion that spans rotation from −5 degrees to +5 degrees, motion blur from 0 to 6 pixels, and noise levels from 0 to 82%. As may be seen, within this sub-space, all inspections passed.

Thus, the machine vision system has been characterized in that it is known under which conditions the system may be expected to operate correctly, i.e., robustly, e.g., within some specified tolerance.

Thus, various embodiments of the above systems and methods may be used to characterize machine vision systems, and may further be used to improve the performance and reliability of vision systems.

Although the embodiments above have been described in considerable detail, numerous variations and modifications will become apparent to those skilled in the art once the above disclosure is fully appreciated. It is intended that the following claims be interpreted to embrace all such variations and modifications.

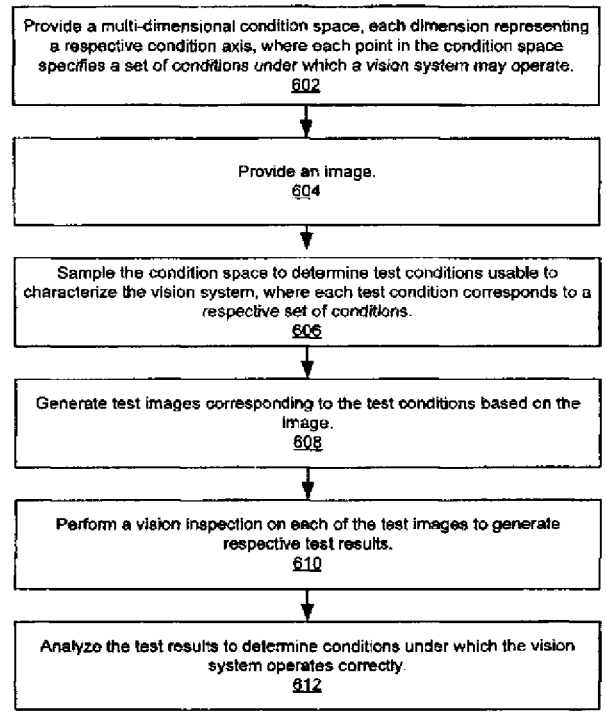

We claim:

1. A computer-implemented method for characterizing a vision system, the method comprising:
providing a condition space comprising a plurality of dimensions, each dimension representing a respective condition axis, wherein each point in the condition space specifies a set of conditions under which a vision system may operate;
providing an image;
sampling the condition space according to a pseudo-random sequence to determine a plurality of test conditions usable to characterize the vision system, wherein each test condition corresponds to a respective set of conditions;
generating a plurality of test images corresponding to the plurality of test conditions based on the image;
performing a vision inspection on each of the plurality of test images to generate respective test results;
analyzing the test results to determine conditions under which the vision system operates correctly; and
storing the test results.

2. The method of claim 1, wherein the condition axes of the condition space comprise axes related to one or more of:
image object geometry;
camera geometry;
lighting;
focus blur;
motion blur; or
noise.

3. The method of claim 2, wherein the condition axes related to image object geometry comprise axes for one or more of:
object scale;
object rotation; or
object offset.

4. The method of claim 2, wherein the condition axes related to camera geometry comprise axes for one or more of:
camera position;
look at position;
camera pan; or
camera rotation.

5. The method of claim 2, wherein the condition axes related to lighting comprise axes for one or more of:
brightness;
contrast; or
gamma.

6. The method of claim 2, wherein the condition axes related to motion blur comprise axes for one or more of:
length of blur; or
angle of blur.

7. The method of claim 2, wherein the condition axes related to noise comprise axes for one or more of:
noise type, comprising: uniform, Gaussian, and/or impulse;
standard deviation; or
amount of noise.

8. The method of claim 1, wherein said generating a plurality of test images corresponding to the plurality of test conditions based on the image comprises:
generating the plurality of test images by applying image processing functions to the image that simulate the plurality of test conditions.

9. The method of claim 8, wherein said generating a plurality of test images corresponding to the plurality of test conditions based on the image comprises:
receiving user input to a graphical user interface specifying one or more of:
test conditions to simulate;
number of samples of the condition space to use; or
range values for one or more of the condition axes.

10. The method of claim 1, wherein said sampling the condition space, said generating the plurality of test images, and said performing a vision inspection on each of the plurality of test images comprises:
for each of a plurality of iterations:
a) sampling the condition space to generate a condition point;
b) generating a test image based on the condition point;
c) performing a vision inspection on the test image;
d) if the vision inspection fails, performing a) - c) for one or more condition points in a specified neighborhood of the condition point to determine a point for which the vision inspection passes.

11. The method of claim 1, wherein said sampling the condition space, said generating the plurality of test images, and said performing a vision inspection on each of the plurality of test images comprises:
for each of a plurality of iterations:
a) sampling the condition space to generate a condition point;
b) generating a test image based on the condition point;
c) performing a vision inspection on the test image;
d) if the vision inspection fails,
e) modifying parameters of the vision inspection;
f) performing a vision inspection on the test image using the modified parameters; and
g) performing e)-f) in an iterative manner until the vision inspection passes.

12. The method of claim 1, wherein said analyzing comprises determining one or more of:
fraction of passes of the vision inspection within the condition space; or a largest convex hull in the condition space specifying conditions under which vision inspections by the vision system will pass within a specified tolerance.

13. The method of claim 1, wherein the pseudo-random sequence comprises a low-discrepancy sequence.

14. A non-transitory computer accessible memory medium that stores program instructions for characterizing a vision system, wherein the program instructions are executable by a processor to:
provide a condition space comprising a plurality of dimensions, each dimension representing a respective condition axis, wherein each point in the condition space specifies a set of conditions
under which a vision system may operate;
provide an image;
sample the condition space according to a pseudo-random sequence to determine a plurality of test conditions usable to characterize the vision system, wherein each test condition corresponds to a respective set of conditions;
generate a plurality of test images corresponding to the plurality of test conditions based on the image;
perform a vision inspection on each of the plurality of test images to generate respective test results; analyze the test results to determine conditions under which the vision system operates correctly.

15. A computer accessible memory medium that stores program instructions for characterizing a vision system, wherein the program instructions are executable by a processor to:
provide a condition space comprising a plurality of dimensions, each dimension representing a respective condition axis, wherein each point in the condition space specifies a set of conditions under which a vision system may operate;
provide an image;
sample the condition space according to a pseudo-random sequence to determine a plurality of test conditions usable to characterize the vision system, wherein each test condition corresponds to a respective set of conditions;
generate a plurality of test images corresponding to the plurality of test conditions based on the image;
perform a vision inspection on each of the plurality of test images to generate respective test results;
analyze the test results to determine conditions under which the vision system operates correctly.

16. The method of claim 15, wherein the condition axes of the condition space comprise axes related to one or more of:
image object geometry;
camera geometry;
lighting;
focus blur;
motion blur; or
noise.

17. The method of claim 16, wherein the condition axes related to image object geometry comprise axes for one or more of:
object scale;
object rotation; or
object offset.

18. The method of claim 17, wherein the condition axes related to camera geometry comprise axes for one or more of:
camera position;
look at position;
camera pan; or
camera rotation.

19. The method of claim 16, wherein the condition axes related to lighting comprise axes for one or more of:
brightness;
contrast; or
gamma.

20. The method of claim 16, wherein the condition axes related to motion blur comprise axes for one or more of:
length of blur; or
angle of blur.

21. The method of claim 16, wherein the condition axes related to noise comprise axes for one or more of:
noise type, comprising: uniform, Gaussian, and/or impulse;
standard deviation; or
amount of noise.

22. The method of claim 15, wherein said generating a plurality of test images corresponding to the plurality of test conditions based on the image comprises:
generating the plurality of test images by applying image processing functions to the image that simulate the plurality of test conditions.

23. The method of claim 8, wherein said generating a plurality of test images corresponding to the plurality of test conditions based on the image comprises:
receiving user input to a graphical user interface specifying one or more of:
test conditions to simulate;
number of samples of the condition space to use; or range values for one or more of the condition axes.

24. The method of claim 15, wherein said sampling the condition space, said generating the plurality of test images, and said performing a vision inspection on each of the plurality of test images comprises:
for each of a plurality of iterations:
a) sampling the condition space to generate a condition point;
b) generating a test image based on the condition point;
c) performing a vision inspection on the test image;
d) if the vision inspection fails, performing a) - c) for one or more condition points in a specified neighborhood of the condition point to determine a point for which the vision inspection passes.

25. The method of claim 15, wherein said sampling the condition space, said generating the plurality of test images, and said performing a vision inspection on each of the plurality of test images comprises:
for each of a plurality of iterations:
a) sampling the condition space to generate a condition point;
b) generating a test image based on the condition point;
c) performing a vision inspection on the test image; d) if the vision inspection fails,
e) modifying parameters of the vision inspection;
f) performing a vision inspection on the test image using the modified parameters; and
g) performing e)-f) in an iterative manner until the vision inspection passes.

26. The method of claim 15, wherein said analyzing comprises determining one or more of:
fraction of passes of the vision inspection within the condition space; or
a largest convex hull in the condition space specifying conditions under which vision inspections by the vision system will pass within a specified tolerance.

27. The method of claim 15, wherein said sampling comprises:
sampling the condition space according to a pseudo-random sequence.

28. The method of claim 27, wherein the pseudo-random sequence comprises a low-discrepancy sequence.

29. A non-transitory computer accessible memory medium that stores program instructions for characterizing a vision system, wherein the program instructions are executable by a processor to:
provide a condition space comprising three or more dimensions, each dimension representing a respective condition axis, wherein each point in the condition space specifies a set of conditions under which a vision system may operate;
provide an image;
sample the condition space to determine a plurality of test conditions usable to characterize the vision system, wherein each test condition corresponds to a respective set of conditions;
generate a plurality of test images corresponding to the plurality of test conditions based on the image;
perform a vision inspection on each of the plurality of test images to generate respective test results;
analyze the test results to determine conditions under which the vision system operates correctly; and
store the test results.

30. The non-transitory computer accessible memory medium of claim 29, wherein said sampling comprises:
sampling the condition space according to a pseudo-random sequence.

31. The non-transitory computer accessible memory medium of claim 30, wherein the pseudo-random sequence comprises a low-discrepancy sequence.

32. The non-transitory computer accessible memory medium of claim 29, wherein the condition axes of the condition space comprise axes related to one or more of:
image object geometry;
camera geometry;
lighting;
focus blur;
motion blur; or
noise.

33. The non-transitory computer accessible memory medium of claim 29, wherein said generating a plurality of test images corresponding to the plurality of test conditions based on the image comprises:
generating the plurality of test images by applying image processing functions to the image that simulate the plurality of test conditions.

34. The non-transitory computer accessible memory medium of claim 33, wherein said generating a plurality of test images corresponding to the plurality of test conditions based on the image comprises:
receiving user input to a graphical user interface specifying one or more of:
test conditions to simulate;
number of samples of the condition space to use; or
range values for one or more of the condition taxes.

35. The non-transitory computer accessible memory medium of claim 29, wherein said sampling the condition space, said generating the plurality of test images, and said performing a vision inspection on each of the plurality of test images comprises:
for each of a plurality of iterations:
a) sampling the condition space to generate a condition point;
b) generating a test image based on the condition point;
c) performing a vision inspection on the test image;
d) if the vision inspection fails, performing a)-c) for one or more condition points in a specified neighborhood of the condition point to determine a point for which the vision inspection passes.

36. The non-transitory computer accessible memory medium of claim 29, wherein said sampling the condition space, said generating the plurality of test images, and said performing a vision inspection on each of the plurality of test images comprises:
for each of a plurality of iterations:
a) sampling the condition space to generate a condition point;
b) generating a test image based on the condition point;
c) performing a vision inspection on the test image;
d) if the vision inspection fails,
e) modifying parameters of the vision inspection;
f) performing a vision inspection on the test image using the modified parameters; and
g) performing e)-f) in an iterative manner until the vision inspection passes.

37. The non-transitory computer accessible memory medium of claim 29, wherein said analyzing comprises determining one or more of:
fraction of passes of the vision inspection within the condition space; or
a largest convex hull in the condition space specifying conditions under which vision inspections by the vision system will pass within a specified tolerance.

\* \* \* \* \*

UNITED STATES PATENT AND TRADEMARK OFFICE
CERTIFICATE OF CORRECTION

| | | |
|---|---|---|
| PATENT NO. | : 8,068,660 B2 | |
| APPLICATION NO. | : 12/127231 | |
| DATED | : November 29, 2011 | |
| INVENTOR(S) | : Nair et al. | |

It is certified that error appears in the above-identified patent and that said Letters Patent is hereby corrected as shown below:

In column 21, lines 52-53, delete "which the vision system operates correctly; and storing the test results." and insert -- which the vision system operates correctly. --.

In column 23, lines 27-47, delete "15. A computer accessible memory medium that stores program instructions for characterizing a vision system, wherein the program instructions are executable by a processor to: provide a condition space comprising a plurality of dimensions, each dimension representing a respective condition axis, wherein each point in the condition space specifies a set of conditions under which a vision system may operate; provide an image; sample the condition space according to a pseudo-random sequence to determine a plurality of test conditions usable to characterize the vision system, wherein each test condition corresponds to a respective set of conditions; generate a plurality of test images corresponding to the plurality of test conditions based on the image; perform a vision inspection on each of the plurality of test images to generate respective test results; analyze the test results to determine conditions under which the vision system operates correctly."
and insert -- 15. A computer-implemented method for characterizing a vision system, the method comprising: providing a condition space comprising three or more dimensions, each dimension representing a respective condition axis, wherein each point in the condition space specifies a set of conditions under which a vision system may operate; providing an image; sampling the condition space to determine a plurality of test conditions usable to characterize the vision system, wherein each test condition corresponds to a respective set of conditions; generating a plurality of test images corresponding to the plurality of test conditions based on the image; performing a vision inspection on each of the plurality of test images to generate respective test results; analyzing the test results to determine conditions under which the vision system operates correctly. --.

In column 23, line 62, delete "The method of claim 17," and insert -- The method of claim 16, --.

In column 24, line 23, delete "The method of claim 8," and insert -- The method of claim 22, --.

Signed and Sealed this
Third Day of April, 2012

David J. Kappos
*Director of the United States Patent and Trademark Office*

CERTIFICATE OF CORRECTION (continued)
U.S. Pat. No. 8,068,660 B2

In column 25, lines 26-27, delete "the condition taxes." and insert -- the condition axes. --.

In column 26, line 9, delete "which the vision system operates correctly; and store the test results." and insert -- which the vision system operates correctly. --.

In column 26, please add -- 38. The method of claim 1, wherein said generating a plurality of test images corresponding to the plurality of test conditions based on the image comprises: generating the plurality of test images by modifying the vision system to produce one or more of the plurality of test conditions. --.

In column 26, please add -- 39. The method of claim 15, wherein said generating a plurality of test images corresponding to the plurality of test conditions based on the image comprises: generating the plurality of test images by modifying the vision system to produce one or more of the plurality of test conditions. --.

UNITED STATES PATENT AND TRADEMARK OFFICE
CERTIFICATE OF CORRECTION

PATENT NO. : 8,068,660 B2  
APPLICATION NO. : 12/127231  
DATED : November 29, 2011  
INVENTOR(S) : Nair et al.

Page 1 of 3

It is certified that error appears in the above-identified patent and that said Letters Patent is hereby corrected as shown below:

Delete the title page and substitute therefore the attached title page showing the corrected number of claims in patent.

In column 21, lines 52-53, delete "which the vision system operates correctly; and storing the test results." and insert -- which the vision system operates correctly. --.

In column 23, lines 27-47, delete "15. A computer accessible memory medium that stores program instructions for characterizing a vision system, wherein the program instructions are executable by a processor to: provide a condition space comprising a plurality of dimensions, each dimension representing a respective condition axis, wherein each point in the condition space specifies a set of conditions under which a vision system may operate; provide an image; sample the condition space according to a pseudo-random sequence to determine a plurality of test conditions usable to characterize the vision system, wherein each test condition corresponds to a respective set of conditions; generate a plurality of test images corresponding to the plurality of test conditions based on the image; perform a vision inspection on each of the plurality of test images to generate respective test results; analyze the test results to determine conditions under which the vision system operates correctly."

and insert -- 15. A computer-implemented method for characterizing a vision system, the method comprising: providing a condition space comprising three or more dimensions, each dimension representing a respective condition axis, wherein each point in the condition space specifies a set of conditions under which a vision system may operate; providing an image; sampling the condition space to determine a plurality of test conditions usable to characterize the vision system, wherein each test condition corresponds to a respective set of conditions; generating a plurality of test images corresponding to the plurality of test conditions based on the image; performing a vision inspection on each of the plurality of test images to generate respective test results; analyzing the test results to determine conditions under which the vision system operates correctly. --.

This certificate supersedes the Certificate of Correction issued April 3, 2012.

Signed and Sealed this  
Eighth Day of May, 2012

David J. Kappos  
*Director of the United States Patent and Trademark Office*

In column 23, line 62, delete "The method of claim 17," and insert -- The method of claim 16, --.

In column 24, line 23, delete "The method of claim 8," and insert -- The method of claim 22, --.

In column 25, lines 26-27, delete "the condition taxes." and insert -- the condition axes. --.

In column 26, line 9, delete "which the vision system operates correctly; and store the test results." and insert -- which the vision system operates correctly. --.

In column 26, please add -- 38. The method of claim 1, wherein said generating a plurality of test images corresponding to the plurality of test conditions based on the image comprises: generating the plurality of test images by modifying the vision system to produce one or more of the plurality of test conditions. --.

In column 26, please add -- 39. The method of claim 15, wherein said generating a plurality of test images corresponding to the plurality of test conditions based on the image comprises: generating the plurality of test images by modifying the vision system to produce one or more of the plurality of test conditions. --.

(12) United States Patent
Nair et al.

(10) Patent No.: US 8,068,660 B2
(45) Date of Patent: Nov. 29, 2011

(54) CHARACTERIZING VISION SYSTEMS

(75) Inventors: Dinesh R. Nair, Austin, TX (US);
Nicolas Vazquez, Austin, TX (US);
Robert J. B. Giesen, Austin, TX (US);
Joshua B. Keeler, Austin, TX (US);
Bruce Smyth, Hollis, NH (US)

(73) Assignee: National Instruments Corporation, Austin, TX (US)

( * ) Notice: Subject to any disclaimer, the term of this patent is extended or adjusted under 35 U.S.C. 154(b) by 772 days.

(21) Appl. No.: 12/127,231

(22) Filed: May 27, 2008

(65) Prior Publication Data
US 2009/0297042 A1    Dec. 3, 2009

(51) Int. Cl.
*G06K 9/00* (2006.01)

(52) U.S. Cl. .................................................. 382/141

(58) Field of Classification Search .......... 382/141–154
See application file for complete search history.

(56) References Cited

U.S. PATENT DOCUMENTS

| | | | |
|---|---|---|---|
| 2003/0007690 A1 * | 1/2003 | Rajagopal et al. | 382/209 |
| 2003/0179922 A1 * | 9/2003 | Peters et al. | 382/153 |
| 2006/0204121 A1 * | 9/2006 | Bryll | 382/255 |
| 2007/0146491 A1 | 6/2007 | Tremblay et al. | |

* cited by examiner

*Primary Examiner* — Michael P Stafira
(74) *Attorney, Agent, or Firm* — Meyertons Hood Kivlin Kowert & Goetzel, P.C.; Jeffrey C. Hood; Joel L. Stevens

(57) ABSTRACT

System and method for characterizing vision systems. A multi-dimensional condition space is provided, each dimension representing a respective condition axis, where each point in the condition space specifies a set of conditions under which a vision system may operate. An image is provided. The condition space is sampled according to a pseudo-random sequence, e.g., a low-discrepancy sequence, to determine a plurality of test conditions usable to characterize the vision system, where each test condition corresponds to a respective set of conditions. A plurality of test images corresponding to the plurality of test conditions are generated based on the image, e.g., by applying image processing functions to the image that simulate the test conditions. A vision inspection is performed on each of the plurality of test images to generate respective test results, and the test results are analyzed to determine conditions under which the vision system operates correctly.

39 Claims, 23 Drawing Sheets